United States Patent
Moore et al.

(10) Patent No.: US 12,121,395 B2
(45) Date of Patent: Oct. 22, 2024

(54) MOUNT FOR ENABLING ONE-HANDED CONTROL OF A MEDICAL DEVICE THAT PROVIDES IMAGING DATA AND AN ELECTRONIC DEVICE DISPLAYING THAT IMAGING DATA, THE MOUNT PROVIDING FOR IN-PLANE AND OUT-OF-PLANE VIEWING CONFIGURATIONS FOR THE ELECTRONIC DEVICE

(71) Applicant: InLine LLC, Lewes, DE (US)

(72) Inventors: Justin Earl Moore, Oakland, CA (US); Arun Daulat Nagdev, San Francisco, CA (US)

(73) Assignee: OcuLine Inc., Lewes, DE (US)

( * ) Notice: Subject to any disclaimer, the term of this patent is extended or adjusted under 35 U.S.C. 154(b) by 21 days.

(21) Appl. No.: 17/229,760

(22) Filed: Apr. 13, 2021

(65) Prior Publication Data

US 2022/0273262 A1    Sep. 1, 2022

Related U.S. Application Data

(60) Provisional application No. 63/154,570, filed on Feb. 26, 2021.

(51) Int. Cl.
*A61B 8/00* (2006.01)

(52) U.S. Cl.
CPC .............. *A61B 8/4209* (2013.01); *A61B 8/46* (2013.01)

(58) Field of Classification Search
None
See application file for complete search history.

(56) References Cited

U.S. PATENT DOCUMENTS

| 6,221,007 B1 | 4/2001 | Green |
| 8,727,290 B1 * | 5/2014 | De La Matta ....... F16M 13/022 379/454 |

(Continued)

FOREIGN PATENT DOCUMENTS

| CN | 107822659 A | 3/2018 |
| KR | 101556205 B1 | 10/2015 |

(Continued)

OTHER PUBLICATIONS

Ashutosh Kaushal et al., Mobile phone holder as an ultrasound transducer stabilization device: A novel technique, Indian Journal of Anesthesia, vol. 62, Issue 8, Aug. 2018, 2 pgs.

(Continued)

*Primary Examiner* — Katherine L Fernandez
*Assistant Examiner* — Farouk A Bruce
(74) *Attorney, Agent, or Firm* — Morgan, Lewis & Bockius LLP

(57) ABSTRACT

A mount for enabling one-handed control of both a medical device and an electronic device. The mount includes a first assembly configured to receive a medical device. The first assembly includes a first member configured to hold the medical device in a fixed position in relation to the first member. The mount includes a second assembly configured to receive the electronic device. The second assembly includes a second member configured to hold the electronic device in a fixed position in relation to the second member. The mount includes a coupling mechanism configured to couple the first and second members such that the first and second members are movable relative to one another. When the first member is holding the medical device and the second member is holding the electronic device, the mount is configured to allow for one-handed movement of the medical device and the electronic device in unison.

16 Claims, 20 Drawing Sheets

(56) References Cited

U.S. PATENT DOCUMENTS

| | | |
|---|---|---|
| 10,352,498 B2 | 7/2019 | Rieger |
| 10,610,194 B2 | 4/2020 | Sonnenschein |
| 2008/0015442 A1 | 1/2008 | Watson et al. |
| 2013/0150714 A1 | 6/2013 | Howlett et al. |
| 2014/0360274 A1* | 12/2014 | Cho .................. G01N 29/0654 73/644 |
| 2015/0038844 A1 | 2/2015 | Blalock et al. |
| 2015/0378143 A1 | 12/2015 | Auguste |
| 2016/0331213 A1 | 11/2016 | Kim |
| 2017/0303857 A1* | 10/2017 | Perkins ............. A61B 1/00052 |
| 2018/0021014 A1 | 1/2018 | Chen et al. |
| 2018/0289355 A1 | 10/2018 | Maracaja |
| 2019/0125064 A1* | 5/2019 | de Jonge ............. A61B 8/4227 |
| 2020/0008673 A1* | 1/2020 | Myung .................. A61B 3/145 |
| 2020/0261057 A1 | 8/2020 | Maracaja |
| 2021/0045712 A1 | 2/2021 | de Jonge et al. |
| 2021/0046885 A1 | 2/2021 | Jankura et al. |
| 2021/0077595 A1 | 3/2021 | Bratbak et al. |
| 2021/0361241 A1 | 11/2021 | Perkins et al. |
| 2021/0369240 A1* | 12/2021 | Moss, Jr. ............. A61B 8/0841 |
| 2022/0061806 A1 | 3/2022 | Burkholz |
| 2022/0133270 A1 | 5/2022 | Maracaja |
| 2023/0101257 A1* | 3/2023 | Poland .................. A61B 8/462 600/437 |

FOREIGN PATENT DOCUMENTS

| | | |
|---|---|---|
| KR | 20180116605 A | 10/2018 |
| WO | WO2020/160550 A1 | 8/2020 |
| WO | WO2021/018271 A1 | 2/2021 |

OTHER PUBLICATIONS

Luiz Maracaja, One Hand and One Eyesight Real-Time Ultrasound Guidance: The Use of CAD Design and 3D Printing for Development of New Tools to Improve Vascular Access, Journal of Cardiothoracic and Vascular Anesthesia 34 (2020), 2136-2139, 4 pgs.

Moore, Justin Earl, International Search Report and Written Opinion, PCT/US2022/018181, Jun. 1, 2022, 13 pgs.

* cited by examiner (A)
↓

702
Perform a first medical procedure with one hand, the first medical procedure including:

704
Providing a mount configured to enable one-handed control of both a medical device and a handheld electronic device, the mount holding the medical device and the handheld electronic device, and configured to allow for one-handed movement of the medical device and the electronic device in unison, the mount including:

706
A first assembly configured to receive the medical device, the medical device configured to provide imaging data of a patient to the handheld electronic device having a display, the first assembly including a first member configured to hold the medical device in a fixed position in relation to a portion of the first member

708
A second assembly configured to receive the electronic device, the electronic device configured to display the imaging data of the patient received from the medical device, the second assembly including a second member configured to hold the electronic device in a fixed position in relation to a portion of the second member

710
The electronic device is positioned above the medical device such that an operator of the mount is able to continue viewing the imaging data of the patient on the display of the electronic device during the one-handed movement

712
A coupling mechanism configured to couple the first assembly to the second assembly such that the first and second members are movable relative to one another

714
Operating the mount to perform the first medical procedure includes moving or holding the medical device and the electronic device together in one hand while using the other hand opposite the one hand to ergonomically perform the second medical procedure

716
When the first member is holding the medical device and the second member is holding the electronic device, operating the mount to perform the first medical procedure includes holding and moving the medical device to enable the one-handed movement of the medical device and the electronic device in unison

718-a
While performing the first medical procedure with one hand, adjusting a position of one or more of the medical device and the electronic device, adjusting the position of the one or more of the medical device and the electronic device including, at the mount, one or more of:

718-b
Adjusting the medical device in the first member

718-c
Adjusting the electronic device in the second member

718-d
Adjusting the first assembly relative to one or more of the second assembly and the coupling mechanism

718-e
Adjusting the second assembly relative to one or more of the first assembly and the coupling mechanism and

718-f
Securing, via the coupling mechanism, an adjusted position of one or more of the first assembly and the second assembly

720
A dimension of the first member is adjustable to one of at least three different predefined positions

722
The dimension of the first member is adjustable using one or more of an adjustable body, Velcro, one or more magnets, a clamp, a slider, and a vise

724
A dimension of the second member is adjustable to one of at least three different predefined positions

726
The dimension of the second member is adjustable using one or more of an adjustable body, Velcro, one or more magnets, a clamp, a slider, and a vise

728
Perform a second medical procedure with another hand opposite the one hand, the second medical procedure performed concurrently with the first medical procedure

730
Performing the second medical procedure includes utilizing the imaging data of the patient displayed by the handheld electronic device to complete the second medical procedure

↓

732-a
The first member and second member include a respective release mechanism, and the method further includes:

732-b
Receiving an input at the respective release mechanism to release one or more of the medical device and the electronic device from being held by the respective member; and

732-c
In response to receiving the input, releasing one or more of the medical device and the electronic device

734
The input includes one or more of actuating a button on the respective member, actuating a switch, providing a signal via the electronic device, and providing a signal via the medical device

736
The respective release mechanisms include one or more of a spring-loaded release, detachable surfaces, attachable surfaces, and actuators Before performing the first medical procedure with one hand, at the mount:
738-a
Providing the medical device to the first assembly;
738-b
Securing the medical device to the first assembly;
738-c
Providing the electronic device to the second assembly;
738-d
Securing the electronic device to the second assembly; and
738-e
Securing the coupling mechanism such that the first member and the second member have a fixed position relative to one another.

802
Form a first assembly configured to receive the medical device, the medical device configured to provide imaging data of a patient to the handheld electronic device having a display, the first assembly including a first member configured to hold the medical device in a fixed position in relation to a portion of the first member

804
Forming one or more of an adjustable body, Velcro, one or more magnets, a clamp, a slider, and a vise operable with the first member such that dimensions of the first member are adjustable to at least three different positions based on dimensions of the medical device

806
Forming a release mechanism operable with the first member, the release mechanism configured to release the medical device from being held by the first member

808
Form a second assembly configured to receive the electronic device, the electronic device configured to display the imaging data of the patient received from the medical device, the second assembly including a second member configured to hold the electronic device in a fixed position in relation to a portion of the second member

810
Forming one or more of an adjustable body, Velcro, one or more magnets, a clamp, a slider, and a vise operable with the second member such that dimensions of the second member are adjustable to at least three different positions based on dimensions of the electronic device

812
Forming a release mechanism operable with the second member, the release mechanism configured to release the electronic device from being held by the second member (A)

Figure 8A (A)

814
Form a coupling mechanism configured to couple the first member to the second member such that the first and second members are movable relative to one another

816
Including one or more of a screw, a nut, a clamp, a vise, a magnet, and a metallic plate in the coupling mechanism

818
Forming a first coupling mechanism that is part of the first assembly and a second coupling mechanism that is part of the second assembly, the first and second coupling mechanisms including one or more of a male connector, a female connector, a magnet, a vice, a clamp, a screw, and a nut

820
Forming a release mechanism operable with the coupling mechanism, the release mechanism configured to release the first assembly and the second assembly from being coupled together

822
The first member holding the medical device and the second member is holding the electronic device such that the mount is configured to allow for one-handed movement of the medical device and the electronic device in unison

824
The first assembly, the second assembly, and the coupling mechanism are formed as a unitary piece

826
The first assembly, the second assembly, and the coupling mechanism are formed as individual components

Figure 8B

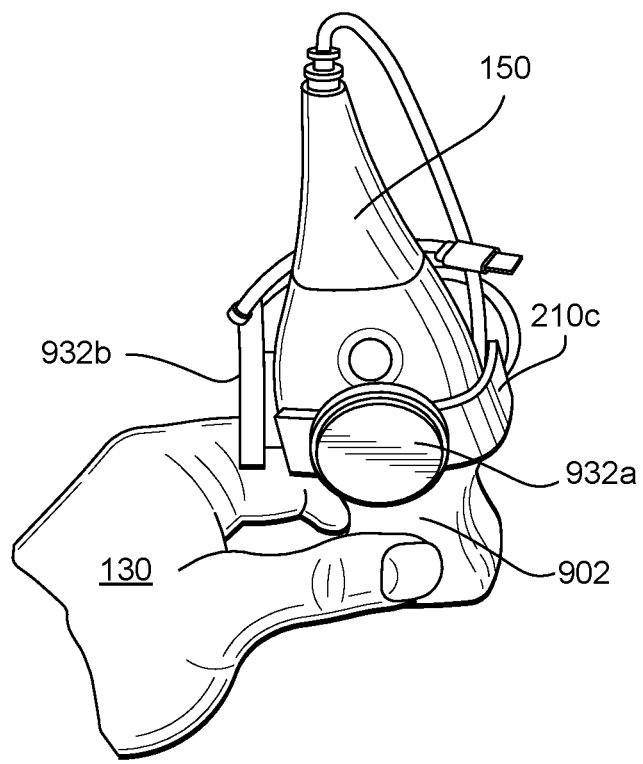
Figure 9A1
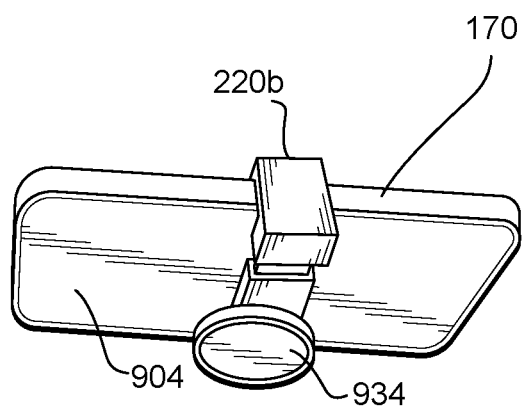
Figure 9A2

MOUNT FOR ENABLING ONE-HANDED CONTROL OF A MEDICAL DEVICE THAT PROVIDES IMAGING DATA AND AN ELECTRONIC DEVICE DISPLAYING THAT IMAGING DATA, THE MOUNT PROVIDING FOR IN-PLANE AND OUT-OF-PLANE VIEWING CONFIGURATIONS FOR THE ELECTRONIC DEVICE

RELATED APPLICATIONS

This application claims priority from U.S. Provisional Application No. 63/154,570, which is incorporated by reference herein for all purposes.

TECHNICAL FIELD

The present disclosure relates generally to systems and devices for removably mounting two distinct electronic devices together to enable one-handed control of both devices, and more particularly to mounts for coupling a medical device (e.g., an ultrasound probe) with an electronic device (e.g., a smartphone displaying imaging data from the example ultrasound probe), and methods of use thereof, which can enable operators to move the medical device and electronic device with one hand while keeping the other hand free (e.g., to view imaging data while also performing a medical procedure with the other hand).

BACKGROUND

Traditionally, ultrasound machines have been large machines on a large base that can be cumbersome and difficult to move around a small hospital room. Advances in technology have made it possible for machines to become smaller and more portable. Handheld probes will soon replace their larger predecessors in many applications. As one example, handheld ultrasound probes have emerged and those rely on the display of a connected device (e.g., a smartphone) to display patient information to medical practitioners, nurses, or other health care providers. These handheld devices require a health care provider to use both hands during device operation—one hand to hold the ultrasound probe and the other to hold the smartphone device. With both healthcare practitioner's hands in use, performing ultrasound-guided procedures (e.g., peripheral IVs, central lines, nerve blocks, etc.) can be challenging and unsafe.

As such, it would be desirable to provide systems, devices, and methods for coupling at least two electronic devices in a mount for one-handed movement in unison to address the above-mentioned drawbacks.

SUMMARY

The mount systems and methods of use and construction thereof described herein make it possible for a user to operate at least two electronic devices (e.g., a smartphone and a medical device, such as an ultrasound probe) with a single hand. For example, the mount systems and methods of use and construction thereof described herein couple the at least two electronic devices together such that the user can move the at least two electronic devices in unison with one hand, a display of at least one electronic device is visible to the user, and the at least two electronic devices operate without interfering with one another. For purposes of this disclosure, a user can be a medical practitioner (e.g., physician, surgeon, etc.), medical support staff (e.g., nurses, technicians, etc.), and/or other health care providers.

By directly coupling the at least two electronic devices together to allow them to move together in unison, the mount systems and devices described herein allow a user to perform a first task with one hand (e.g., to position a first electronic device, such an handheld ultrasound probe in a desired position while watching imaging data from the handheld ultrasound probe being displayed on a screen of a second electronic device, such as a smartphone that is communicatively coupled with the handheld ultrasound probe and also mounted together with the handheld ultrasound probe by way of the inventive mount described herein) using the at least two electronic devices while leaving the other hand free to perform other tasks (e.g., to ergonomically perform a medical procedure such as inserting an IV under ultrasound guidance). The mount systems securely couple the at least two electronic devices together to minimize incidental movement of each device, while allowing for quick detachment of each electronic device as needed. The mount systems fit electronic devices of varying shapes and sizes (e.g., capable of securely holding electronic devices of many different brands and manufacturers) and allow the at least two electronic devices to be oriented and/or adjusted in various positions while mounted. The mount systems also improve the ergonomic operation of the at least two electronic devices, for example, by minimizing awkward body positions and/or movements in holding each electronic device and/or repositioning to view a display).

Further, the mount systems and devices can be a unitary structure (e.g., a mount with only a first assembly 210c that has an included magnetic-connection component (e.g. magnetic coupling mechanisms 932a) that can be directly coupled to a smartphone via magnetic attraction, FIG. 9A1), can be formed of two or more constituent components (e.g., a mount can include the first assembly 210c that can also be coupled with a second assembly 220b that has a separate magnetic connection component (magnetic coupling mechanisms 934) for smartphones that might lack their own magnetic connections, FIG. 9A2; and also a mount can include the first assembly 210a-210b and the second assembly 220a, which are shown in FIGS. 2A-3C and 5A-6). In still other embodiments, the magnetic connection component can be directly integrated with a medical device (e.g., the ultrasound probe 150, FIG. 9A1) such that no separate structure is needed and smartphones having included magnetic connections can then be directly coupled to the housing of the medical device 150 through a magnetic attractive force. These example embodiments are each discussed in detail below.

(A1) In accordance with some embodiments, a mount for enabling one-handed control of both a medical device and a handheld electronic device is provided. The mount includes a first assembly configured to receive a medical device. The medical device is configured to provide imaging data of a patient to an electronic device having a display. The first assembly includes a first member configured to hold the medical device in a fixed position in relation to a portion of the first member. The mount includes a second assembly configured to receive the electronic device. The electronic device is configured to display the imaging data of the patient received from the medical device. The second assembly includes a second member configured to hold the electronic device in a fixed position in relation to a portion of the second member. The mount further includes a coupling mechanism configured to couple the first member to the second member such that the first and second members are movable relative to one another. When the first member is holding the medical device and the second member is holding the electronic device, the mount is configured to allow for one-handed movement of the medical device and the electronic device in unison.

(A2) In some embodiments of (A1), by allowing for one-handed movement of the medical device and the electronic device in unison, an operator of the mount is able to move or hold the medical device and the electronic device together in one hand while using the operator's other hand to ergonomically perform a medical procedure.

(A3) In some embodiments of any of (A1)-(A2), when the first member is holding the medical device and the second member is holding the electronic device, the mount is configured to allow an operator to hold and move the medical device to enable the one-handed movement of the medical device and the electronic device in unison.

(A4) In some embodiments of any of (A1)-(A3), during the one-handed movement of the medical device and the electronic device, the mount is configured to position the electronic device above the medical device such that an operator of the mount is able to continue viewing the imaging data of the patient on the display of the electronic device during the one-handed movement.

(A5) In some embodiments of any of (A1)-(A4), the medical device is an ultrasound probe (e.g., a handheld ultrasound probe that does not have its own associated display device and is instead configured to display imaging data from the probe on a separate device, such as a smartphone or tablet device that is communicatively coupled with the probe).

(A6) In some embodiments of any of (A1)-(A5), a dimension of the first member (e.g., a width between respective sides of the first member) is adjustable to one of at least three different predefined positions, each of the at least three different predefined positions associated with a respective medical device having at least one dimension (e.g., a width of the medical device) that substantially matches a dimension of a respective predefined position of the first member.

(A6.5) In some embodiments of any of (A1)-(A5), a dimension of the first member is adjustable along a sliding scale of values (in other words, the dimension of the first member can be flexibly defined and is not limited to a set of predefined positions).

(A7) In some embodiments of any of (A6) or (A6.5), the dimension of the first member is adjustable using one or more of an adjustable body, Velcro, one or more magnets, a clamp, a slider, and a vise.

(A8) In some embodiments of any of (A1)-(A7), the first member includes a release mechanism configured to release the medical device from being held by the first member.

(A9) In some embodiments of any of (A1)-(A8), the mount includes a cable-management component configured to hold a cable that communicatively connects the medical device to the electronic device to enable the medical device to provide its imaging data to the electronic device (as described in more detail below, in other embodiments, the communicative coupling between the medical device and the electronic device can be accomplished in a wireless fashion such that these other embodiments of the mount would not then need the cable-management component). The cable can be configured to convey the imaging data from the medical device to the electronic device.

(A10) In some embodiments of any of (A1)-(A9), the electronic device is a smartphone or a tablet.

(A11) In some embodiments of any of (A1)-(A10), a dimension of the second member is adjustable to one of at least three different predefined positions based on dimensions of the electronic device, each of the at least three different predefined positions associated with a respective electronic device having at least one dimension (e.g., a width of the electronic device) that substantially matches a dimension of a respective predefined position of the second member.

(A12) In some embodiments of (A11), the dimension of the second member is adjustable using one or more of an adjustable body, Velcro, one or more magnets, a clamp, a slider, and a vise.

(A13) In some embodiments of any of (A1)-(A12), the second member includes a release mechanism configured to release the electronic device from being held by the second member.

(A14) In some embodiments of any of (A1)-(A13), the second member holds the electronic device in the fixed position in relation to a portion of the second member via a magnetic force.

(A15) In some embodiments of any of (A1)-(A14), the coupling mechanism includes one or more of a screw, a nut, a clamp, a vise, a magnet, and a metallic plate.

(A16) In some embodiments of any of (A1)-(A15), the coupling mechanism includes a first coupling mechanism that is part of the first assembly and a second coupling mechanism that is part of the second assembly. The first and second coupling mechanisms including one or more of a male connector, a female connector, a magnet, a vice, a clamp, and a screw.

(A17) In some embodiments of any of (A1)-(A16), the mount is configured to perform (or to be used in conjunction with performance of) any of the methods of (B1)-(B14) described below.

(B1) In accordance with some embodiments, a method of performing medical procedures concurrently includes performing a first medical procedure with one hand. Performing the first medical procedure includes operating a mount configured to enable one-handed control of both a medical device and a handheld electronic device. The mount holds the medical device and the handheld electronic device. The mount is configured to allow for one-handed movement of the medical device and the electronic device in unison. The mount includes a first assembly configured to receive the medical device. The medical device is configured to provide imaging data of a patient to the handheld electronic device having a display. The first assembly includes a first member configured to hold the medical device in a fixed position in relation to a portion of the first member. The mount includes a second assembly configured to receive the electronic device. The electronic device is configured to display the imaging data of the patient received from the medical device. The second assembly includes a second member configured to hold the electronic device in a fixed position in relation to a portion of the second member. The mount further includes a coupling mechanism configured to couple the first member to the second member such that the first and second members can be movable or fixed relative to one another. The method further includes performing a second medical procedure with another hand opposite the one hand, the second medical procedure performed concurrently with the first medical procedure.

(B2) In some embodiments of (B1), performing the second medical procedure includes utilizing the imaging data of the patient displayed by the handheld electronic device to complete the procedure (e.g., place the medical device in a desired position of a patient's body so that the second medical procedure can then be performed using the imaging data from the medical device for guidance during the second medical procedure).

(B3) In some embodiments of any of (B1)-(B2), the method further includes before performing the first medical procedure with one hand, at the mount providing the medical device to the first assembly, securing the medical device to the first assembly, providing the electronic device to the second assembly, securing the electronic device to the second assembly, and securing the coupling mechanism such that the first member and the second member have a fixed position relative to one another.

(B4) In some embodiments of any of (B1)-(B3), the method further includes while performing the first medical procedure with one hand, adjusting a position of one or more of the medical device and the electronic device. Adjusting the position of the one or more of the medical device and the electronic device includes, at the mount, one or more of adjusting the medical device in the first member, adjusting the electronic device in the second member, adjusting the first assembly relative to one or more of the second assembly and the coupling mechanism, adjusting the second assembly relative to one or more of the first assembly and the coupling mechanism, and securing, via the coupling mechanism, an adjusted position of one or more of the first assembly and the second assembly.

(B5) In some embodiments of any of (B1)-(B4), a dimension of the first member (e.g., a width between respective sides of the first member) is adjustable to one of at least three different predefined positions, each of the at least three different predefined positions associated with a respective medical device having at least one dimension (e.g., a width of the medical device) that substantially matches a dimension of a respective predefined position of the first member.

(B5.5) In some embodiments of any of (B1)-(B4), a dimension of the first member is adjustable along a sliding scale of values (in other words, the dimension of the first member can be flexibly defined and is not limited to a set of predefined positions).

(B6) In some embodiments of (B5) or (B.5), the dimension of the first member is adjustable using one or more of an adjustable body, Velcro, one or more magnets, a clamp, a slider, and a vise.

(B7) In some embodiments of any of (B1)-(B6), a dimension of the second member is adjustable to one of at least three different predefined positions based on dimensions of the electronic device, each of the at least three different predefined positions associated with a respective electronic device having at least one dimension (e.g., a width of the electronic device) that substantially matches a dimension of a respective predefined position of the second member.

(B8) In some embodiments of (B7), the dimension of the second member is adjustable using one or more of an adjustable body, Velcro, one or more magnets, a clamp, a slider, and a vise.

(B9) In some embodiments of any of (B1)-(B8), operating the mount to perform the first medical procedure includes moving or holding the medical device and the electronic device together in one hand while using the other hand opposite the one hand to ergonomically perform the second medical procedure.

(B10) In some embodiments of any of (B1)-(B9), when the first member is holding the medical device and the second member is holding the electronic device, operating the mount to perform the first medical procedure includes holding and moving the medical device to enable the one-handed movement of the medical device and the electronic device in unison.

(B11) In some embodiments of any of (B1)-(B10), the electronic device is positioned above the medical device such that an operator of the mount is able to continue viewing the imaging data of the patient on the display of the electronic device during the one-handed movement.

(B12) In some embodiments of any of (B1)-(B11), the first member and second member include a respective release mechanism, and the method further includes receiving an input at the respective release mechanism to release one or more of the medical device and the electronic device from being held by the respective member, and in response to receiving the input, releasing one or more of the medical device and the electronic device.

(B13) In some embodiments of (B12), the input includes one or more of actuating a button on the respective member, actuating a switch, providing a signal via the electronic device, and providing a signal via the medical device.

(B14) In some embodiments of any of (B12)-(B13), the respective release mechanisms include one or more of a spring-loaded release, detachable surfaces, attachable surfaces, and actuators.

(C1) In accordance with some embodiments, a system for coupling a medical device and a handheld electronic device is provided. The system includes a mount for enabling one-handed control of both a medical device and a handheld electronic device. The mount is configured to receive the medical device on at a first assembly. The medical device is configured to provide imaging data of a patient to an electronic device having a display. The first assembly includes a first member configured to hold the medical device in a fixed position in relation to a portion of the first member. The mount is further configured to receive the electronic device at a second assembly. The electronic device is configured to display the imaging data of the patient received from the medical device. The second assembly includes a second member configured to hold the electronic device in a fixed position in relation to a portion of the second member. The mount is further configured to couple the first member to the second member via a coupling mechanism such that the first and second members are movable relative to one another. When the first member is holding the medical device and the second member is holding the electronic device, the mount is configured to allow for one-handed movement of the medical device and the electronic device in unison.

(C2) In some embodiments of C1, the mount system is configured to perform (or to be used in conjunction with performance of) any of the methods of (B1)-(B14) described above.

(D1) In accordance with some embodiments, a method of forming a mount for enabling one-handed control of both a medical device and a handheld electronic device includes forming a first assembly configured to receive the medical device. The medical device is configured to provide imaging data of a patient to the handheld electronic device having a display. The first assembly includes a first member configured to hold the medical device in a fixed position in relation to a portion of the first member. The method includes forming a second assembly configured to receive the electronic device. The electronic device is configured to display the imaging data of the patient received from the medical device. The second assembly includes a second member configured to hold the electronic device in a fixed position in relation to a portion of the second member. The method further includes forming a coupling mechanism configured to couple the first member to the second member such that the first and second members are movable relative to one another. When the first member is holding the medical device and the second member is holding the electronic device, the mount is configured to allow for one-handed movement of the medical device and the electronic device in unison.

(D2) In some embodiments of (D1), the first assembly, the second assembly, and the coupling mechanism are formed as a unitary piece.

(D3) In some embodiments of any of (D1)-(D2), the first assembly, the second assembly, and the coupling mechanism are formed as individual components.

(D4) In some embodiments of any of (D1)-(D3), forming the coupling mechanism includes including one or more of a screw, a nut, a clamp, a vise, a magnet, and a metallic plate in the coupling mechanism.

(D5) In some embodiments of any of (D1)-(D4), forming the coupling mechanism includes forming a first coupling mechanism that is part of the first assembly and a second coupling mechanism that is part of the second assembly. The first and second coupling mechanisms include one or more of a male connector, a female connector, a magnet, a vice, a clamp, and a screw.

(D6) In some embodiments of any of (D1)-(D5), forming the coupling mechanism includes forming a release mechanism operable with the coupling mechanism. The release mechanism is configured to release the first assembly and the second assembly from being coupled together.

(D7) In some embodiments of any of (D1)-(D6), forming the first assembly includes forming one or more of an adjustable body, Velcro, one or more magnets, a clamp, a slider, and a vise operable with the first member such that dimensions of the first member are adjustable to at least three different positions based on dimensions of the medical device.

(D8) In some embodiments of any of (D1)-(D7), forming the first assembly includes forming a release mechanism operable with the first member. The release mechanism is configured to release the medical device from being held by the first member.

(D9) In some embodiments of any of (D1)-(D8), forming the second assembly includes forming one or more of an adjustable body, Velcro, one or more magnets, a clamp, a slider, and a vise operable with the second member such that dimensions of the second member are adjustable to at least three different positions based on dimensions of the electronic device.

(D10) In some embodiments of any of (D1)-(D9), forming the second assembly includes forming a release mechanism operable with the second member. The release mechanism is configured to release the electronic device from being held by the second member.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

So that the present disclosure can be understood in greater detail, a more particular description may be had by reference to the features of various embodiments, some of which are illustrated in the appended drawings. The appended drawings, however, merely illustrate pertinent features of the present disclosure and are therefore not to be considered limiting, for the description may admit to other effective features as the person of skill in this art will appreciate upon reading this disclosure.

FIGS. 7A-7C are flow diagrams showing a method of performing medical procedures concurrently, in accordance with some embodiments.

FIGS. 8A and 8B are flow diagram showing a method of forming a mount, in accordance with some embodiments.

FIGS. 9A1-9C illustrate additional views of a third embodiment of a mount system.

Figure 1A:
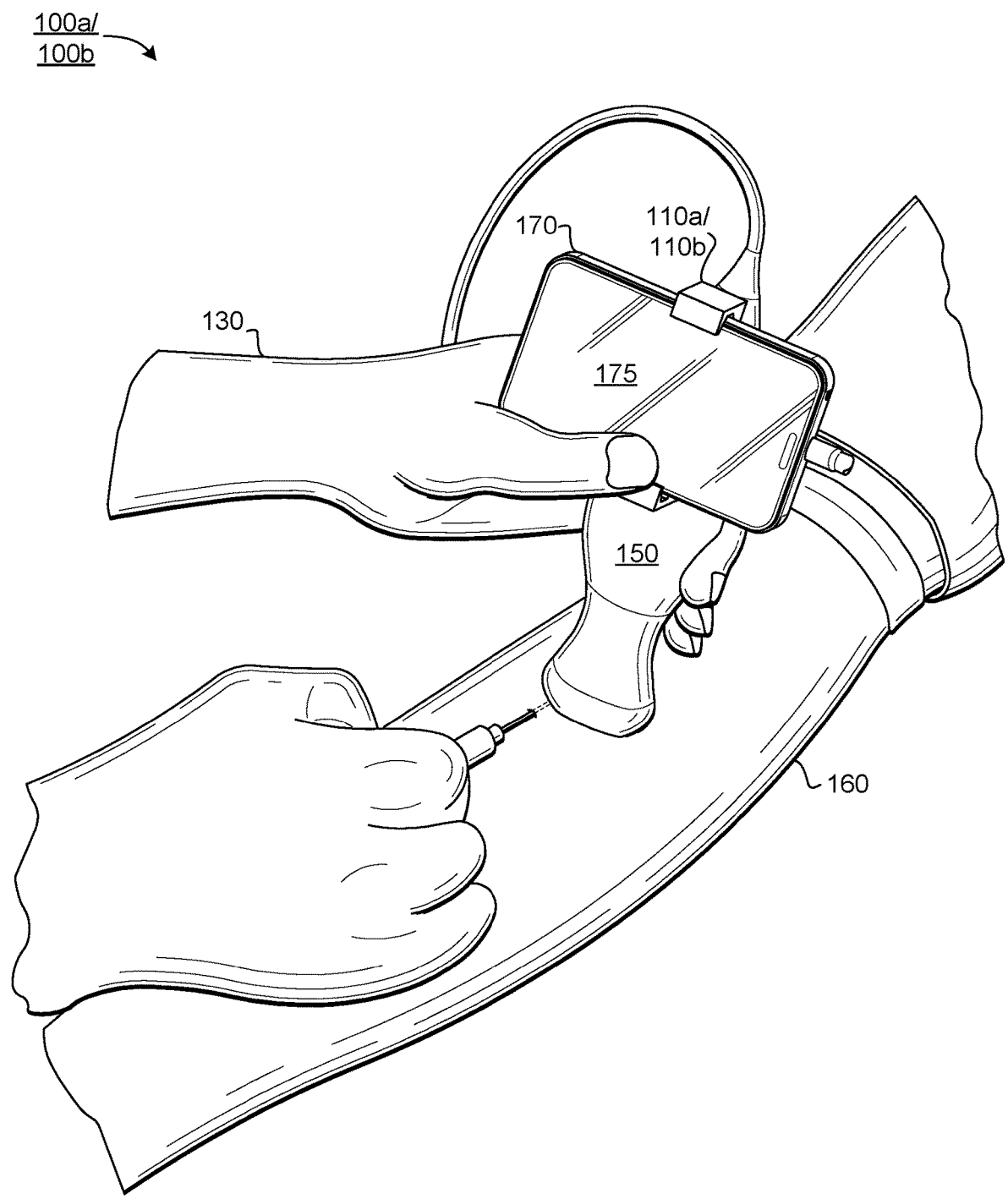
FIG. 1A illustrates an overview of a first embodiment and a second embodiment of a mount system that can be used in conjunction with ergonomic performance of medical procedures.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Numerous details are described herein in order to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not been described in exhaustive detail so as not to unnecessarily obscure pertinent aspects of the embodiments described herein.

FIG. 1A illustrates an overview of a first embodiment and a second embodiment of a mount system 100a/100b. In FIG. 1, the mount system 100a and 100b include one or more of a first or a second embodiment of a mount 110a/110b, a medical device 150, and an electronic device 170. The medical device 150 can be an ultrasound probe, a laser probe, an EKG machine, and/or other portable medical device. The medical device 150 is configured to provide imaging data (or other data collected by the medical device 150) of a patient 160 to an electronic device 170 having a display 175. The electronic device 170 can be a phone, a tablet, a PDA, a controller, and/or other handheld devices with a display. The electronic device 170 is configured to display the imaging data of the patient 160 received from the medical device 150. The first or second embodiments of the mount 110a/110b enable one-handed control of both the medical device 150 and the electronic device 170. More specifically, the first or second embodiments of the mount 110a/110b allows for one-handed movement of the medical device 150 and the electronic device 170 in unison, while allowing the operator's other hand to remain free.

Further, the first or second embodiment of the mount 110a/110b allow a user 130 (also referred to herein as an "operator") to move and/or hold the medical device 150 and the electronic device 170 together in one hand while enabling the user 130 to use their free hand (or opposite hand) to perform one or more additional medical procedures. For example, the first or second embodiment of the mount 110a/110b may hold an ultrasound probe and a smartphone together such that the user 130 has one-handed control of both the ultrasound probe and the smartphone to perform a first medical procedures (e.g., view imaging data of a patient 160) while leaving the other hand of the user 130 free to perform a second medical procedure (e.g., insertion of peripheral IVs or central lines, and can also include nerve block procedures, etc.). The mount system 100 allows for ergonomic use of the medical device 150 and the electronic device 170. Specifically, the first or second embodiments of the mount 110a/110b are configured such that the display 175 of the electronic device 170 is visible to the user 130 without the user 130 having to reposition their body or a portion thereof (e.g., head, torso, etc.), which can otherwise eliminate the user's ability to both view the imaging data and also perform another medical procedure based on the imaging data.

In some embodiments, the first or second embodiments of the mount 110a/110b are configured to allow the user 130 to (one-handedly) move the medical device 150 (and the electronic device 170) to different positions on a patient's body without the medical device 150 losing its ability to continue to collect and provide imaging data to the electronic device 170 for display 175. In some embodiments, during the one-handed movement of the medical device 150 and the electronic device 170, the first or second embodiments of the mount 110a/110b are configured to position the electronic device 170 above the medical device 150 such that the user 130 of the first or second embodiments of the mount 110a/110b are able to continue viewing the imaging data of the patient 160 on the display 175 of the electronic device 170 during the one-handed movement (as described in more detail below, relative positions, such as angles of the devices can also be either adjusted on-the-fly to ensure that the imaging data is viewed at a desired angle by the user, or the angles can be fixed to positions that allow the image data to be viewed at most angles).

Figure 1B:
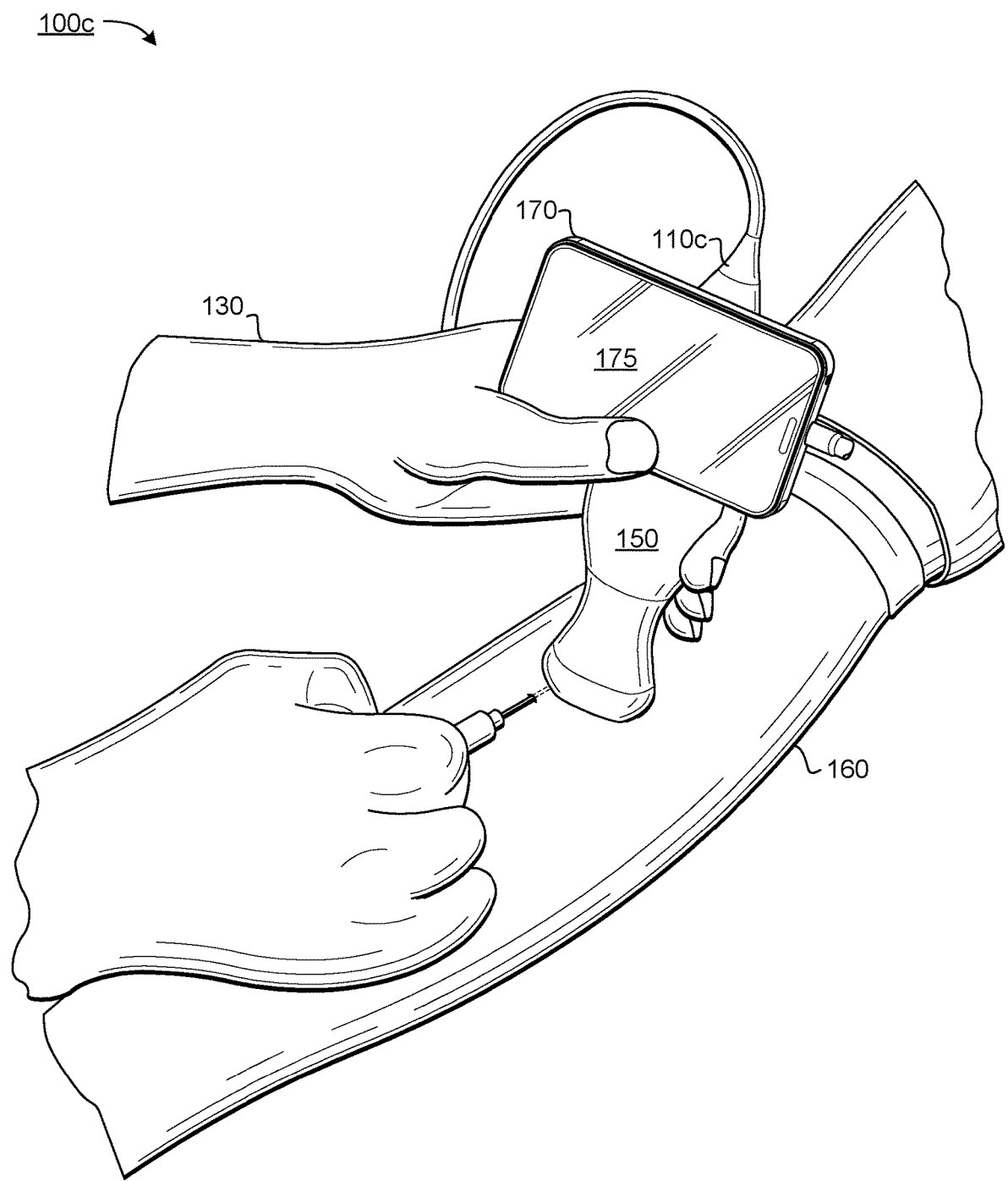
FIG. 1B illustrates an overview of a third embodiment of a mount system that can be used in conjunction with ergonomic performance of medical procedures.

FIG. 1B shows a third embodiment of the mount system 100c, in which a magnetic attractive force can be used to ensure that the electronic device 150 remains coupled to the medical device 150 to allow for one-handed control of both devices in unison. Additional details regarding the third embodiment of the mount system 100c are provided below in reference to FIGS. 9A1-9C.

Figure 2A:
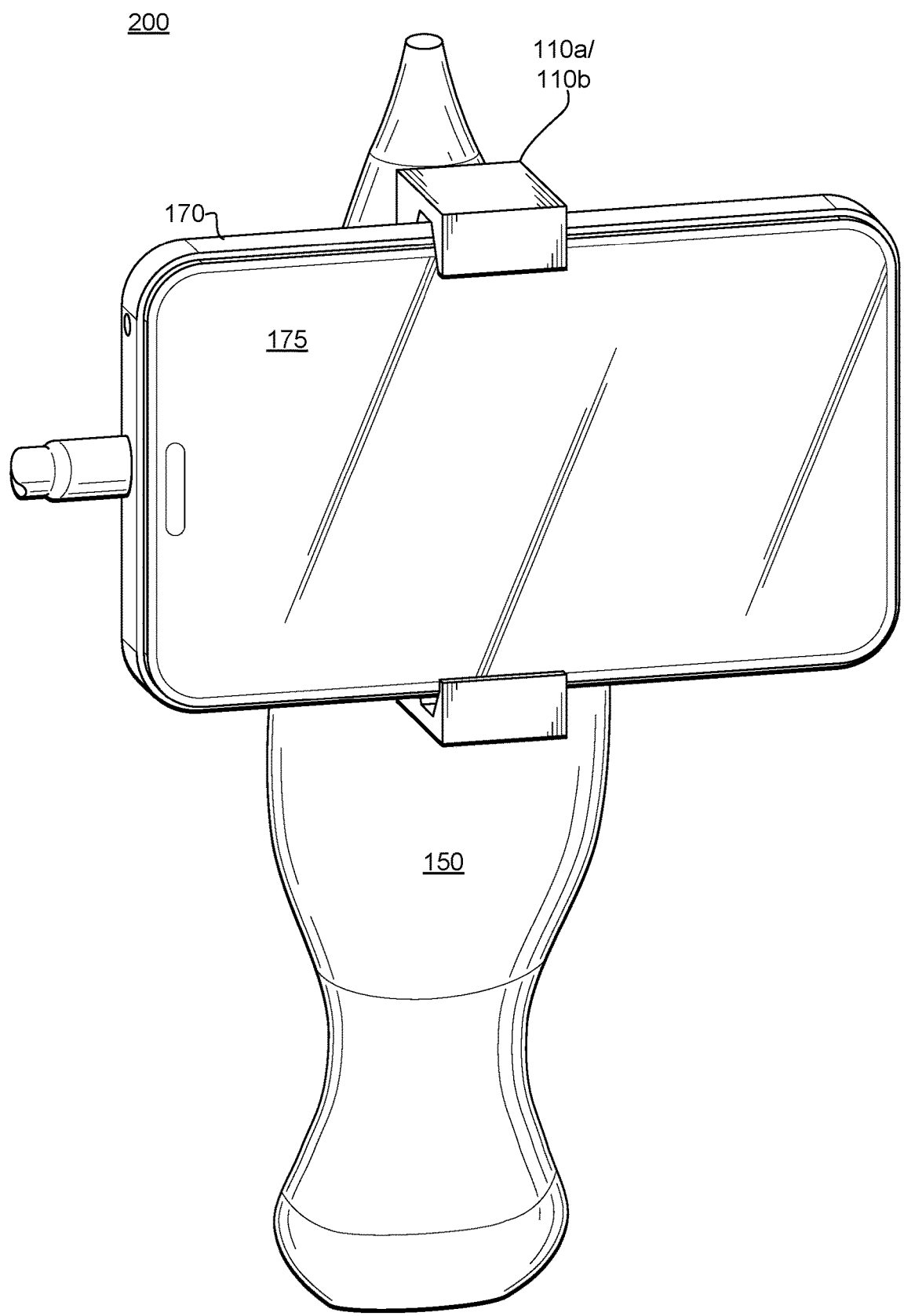
FIGS. 2A-2C illustrate different views of the first embodiment of the mount systems.
Figure 2B:
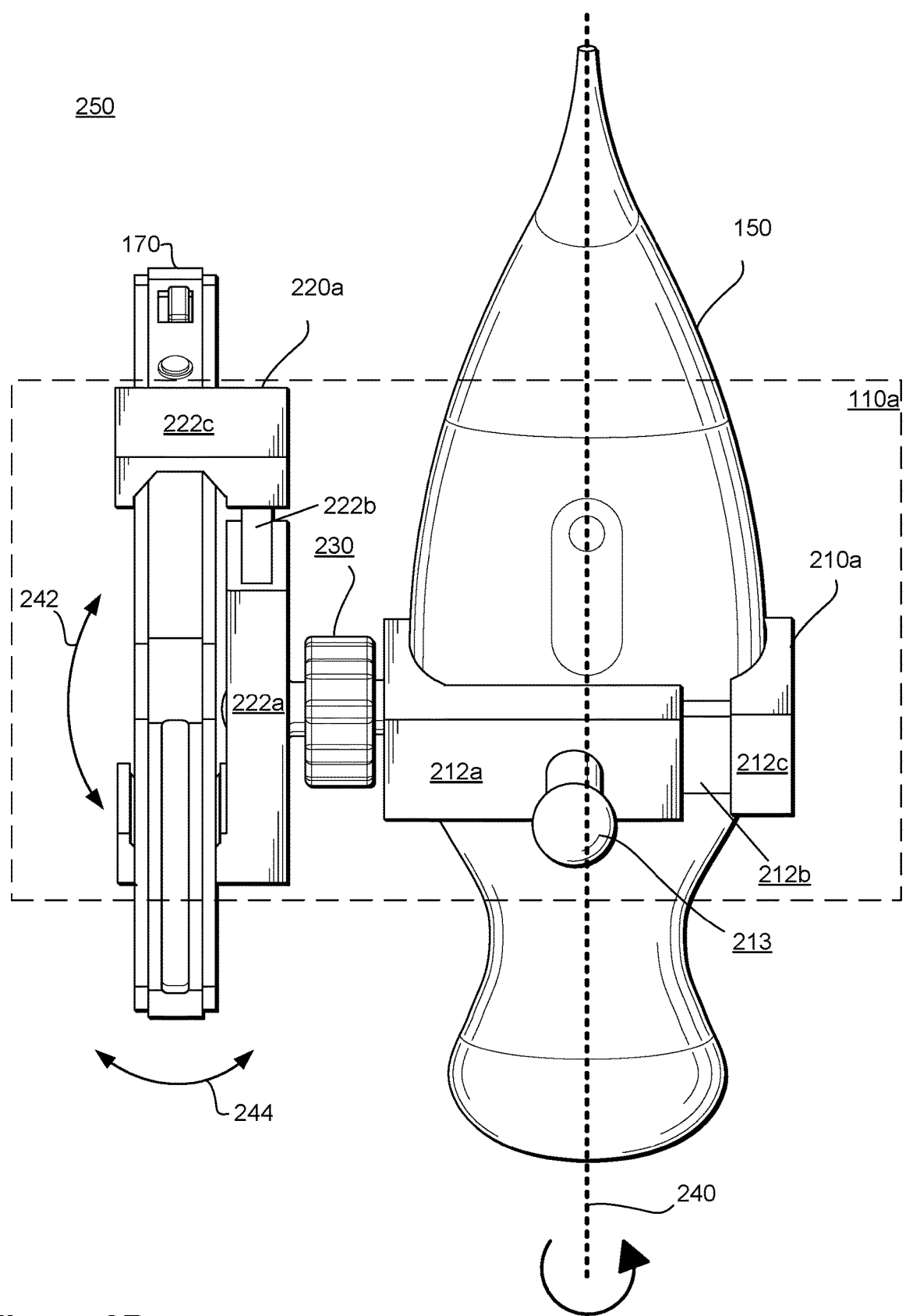
Figure 2C:
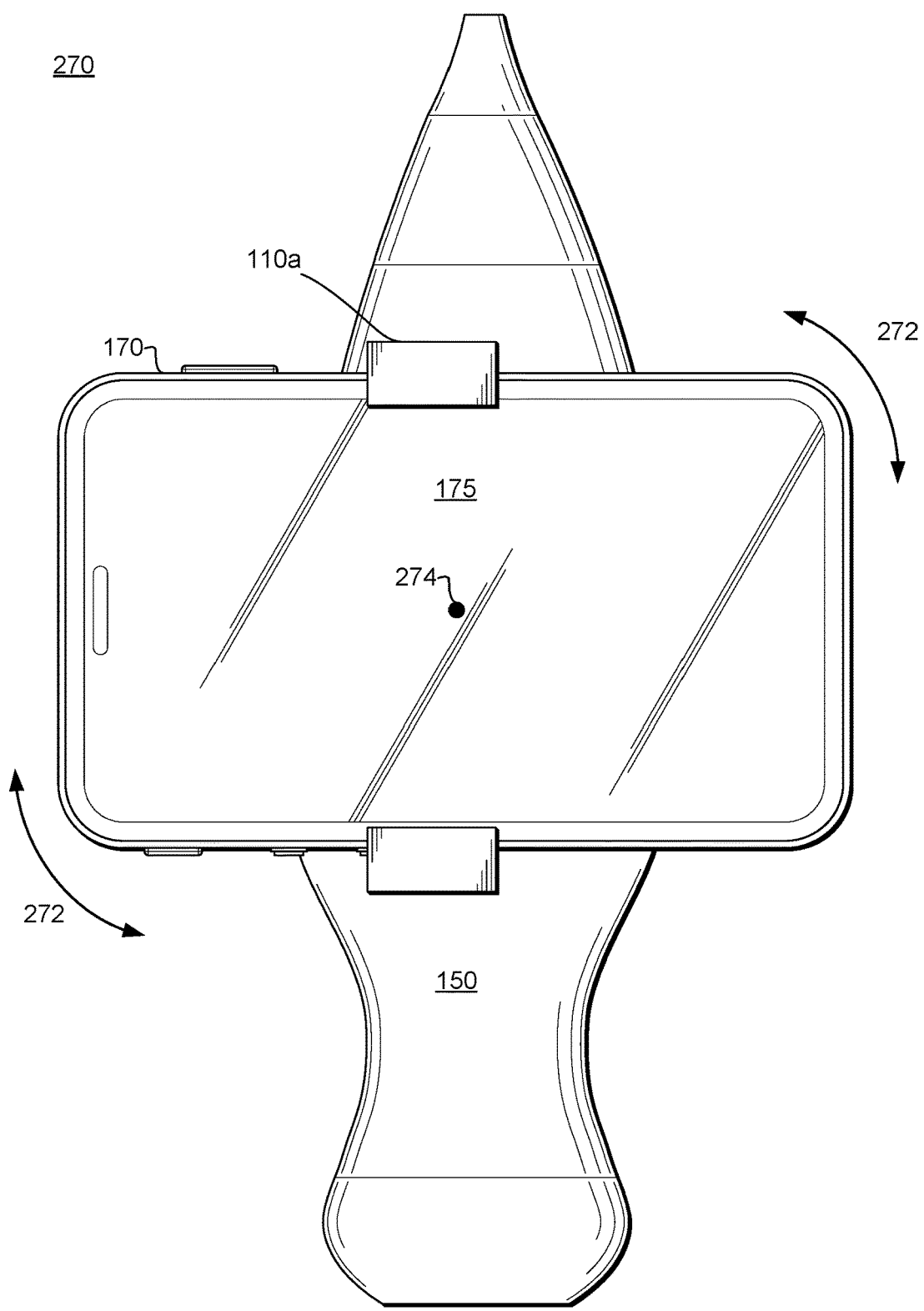

FIGS. 2A-2C illustrate different views of the first embodiment of a mount system 100a. FIG. 2A shows a perspective view 200 of the first embodiment of a mount system 100a. The mount system 100a includes one or more of a first embodiment of a mount 110a, a medical device 150, and an electronic device 170 as described above in FIG. 1. As described above, in the first embodiment of the mount 110a is configured to position the electronic device 170 above the medical device 150 such that the user 130 of the first embodiment of the mount 110a is able to continue viewing the imaging data of the patient 160 (FIG. 1) on the display 175 of the electronic device 170 during the one-handed movement. The first embodiment of the mount 110a is configured to hold the medical device 150 and the electronic device 170 such that each device can perform its regular functions without interfering with one another. For example, the first embodiment of the mount 110a holds the electronic device 170 so that it does not interfere with the data collected by the medical device 150 (e.g., prevents electromagnetic interference, positions the electronic device 170 so that it does not limit the movement of the medical device 150, etc.). Additionally, the first embodiment of the mount 110a is configured such that input and output interfaces of the medical device 150 and the electronic device 170 are accessible to the user 130. For example, the first embodiment of the mount 110a can hold the medical device 150 and the electronic device 170 without obstructing buttons, cameras, sensors, USB ports, audio jacks, etc. of the medical device 150 and the electronic device 170.

FIG. 2B shows a side view 250 of the first embodiment of a mount system 100a. The first embodiment of the mount 110a can include a first assembly 210a configured to receive the medical device 150, a second assembly 220a configured to receive the electronic device 170, and a coupling mechanism 230 configured to couple the first assembly 210a to the second assembly 220a such that one or more portions of the first assembly 210a and one or more portions of the second assembly 220a are movable relative to one another as discussed below.

The first assembly 210a includes a first member formed by one or more first member components 212a-212c configured to hold the medical device 150 in a fixed position in relation to a portion of the first member (e.g., first member component 212a or backplate 312). In some embodiments, the one or more first member components 212a-212c hold the medical device 150 such that the medical device 150 cannot move relative to a portion of the first member (e.g., first member component 212a or backplate 312; shown in FIG. 3B).

The second assembly 220a includes a second member formed by one or more second member components 222a-222c configured to hold the electronic device 170 in a fixed position in relation to a portion of the second member (e.g., second member component 222a or backplate 322). In some embodiments, the second member 222 holds the electronic device 170 such that the electronic device 170 cannot move relative to a portion of the second member (e.g., second member component 222a or backplate 322; shown in FIG. 3B). In some embodiments, when the one or more first member components 212a-212c are holding the medical device 150 and the one or more second member components 222a-222c are holding the electronic device 170, the first embodiments of mount 110a is configured to allow the user 130 to hold and move the medical device 150 to enable the one-handed movement of the medical device 150 and the electronic device 170 in unison.

The first assembly 210a, the second assembly 220a, and the coupling mechanism 230 are discussed in more detail below in reference to FIGS. 3A-3C.

The first embodiment of the mount 110a is configured to hold (via the first assembly 210a) the medical device 150 in different orientations. In particular, the first embodiment of the mount 110a is configured to hold the medical device 150 in different positions when rotated along centerline 240. For example, the first embodiment of the mount 110a can hold the medical device 150 illustrated in side view 250 when rotated 15 degrees, 30 degrees, 45 degrees, 60 degrees, 90 degrees, etc. around center line 240. Additionally, the first embodiment of the mount 110a is configured to hold (via the second assembly 220a) the electronic device 170 in different orientations. For example, the first embodiment of the mount 110a can hold the electronic device 170 in a portrait or landscape orientation.

In other embodiments, a location of the coupling member 230 can be moved to allow for holding the electronic device 170 in either the same plane or a different plane relative to the medical device 150. In the first embodiment of the mount 110a shown in FIG. 2B, the smartphone 170 is held in an "in-plane" position with respect to the medical device 150. In other embodiments, the coupling member 230 can be moved to a different position along the first assembly 210a to instead hold the smartphone assembly 170 in an "out-of-plane" position with respect to the medical device 150 (e.g., the coupling member 230 can be moved to the long edge of the first assembly 210a). The second embodiment discussed below (in reference to FIGS. 9A1-9C) provides an example design in which both "in plane" and "out-of-plane" configurations can be made available in one mount design, which can also be achieved by varying the design of the first embodiment as mentioned above.

As further shown in side view 250, the first embodiment of the mount 110a is configured to allow the position of the medical device 150 and the electronic device 170 to be to be adjusted relative to one another. For example, a position of the medical device 150 relative to the electronic device 170 can be adjusted by a vertical angle 242 such that a user 130 can adjust the position of the medical device 150 and the electronic device 170 as desired. In another example, a position of the medical device 150 relative to the electronic device 170 can be adjusted by a horizontal angle 244 such that the user 130 can adjust the position of the medical device 150 and the electronic device 170 as desired. Adjustments to the position of the medical device 150 and the electronic device 170 are discussed below in FIG. 3A.

In some embodiments, the first embodiment of the mount 110a includes a handle 213 such that the user can ergonomically hold the first embodiment of the mount 110a. The handle 213 can be mounted of the first assembly 210a or the second assembly 210b.

FIG. 2C shows a front view 270 of the first embodiment of mount system 100a, in accordance with some embodiments. As further shown in the front view 270, the first embodiment of the mount 110a is configured to allow the position of the medical device 150 and the electronic device 170 to rotate relative to one another. For example, a position of the medical device 150 relative to the electronic device 170 can be rotated by a central angle 272 such that a user 130 can adjust the position of the medical device 150 and the electronic device 170 as desired. The central angle 272 is rotated around central point 274. Adjustments to the position of the medical device 150 and the electronic device 170 are discussed below in FIG. 3A.

Figure 3A:
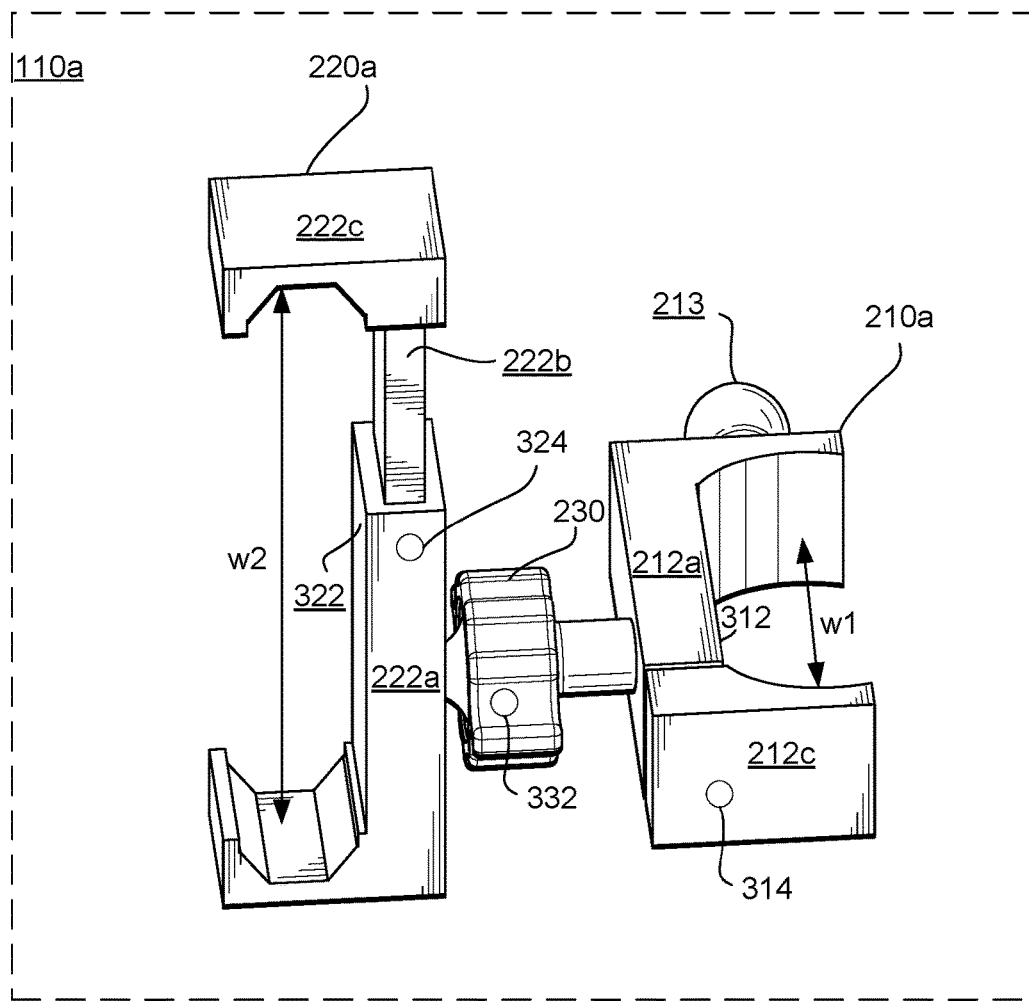
FIG. 3A-3C illustrate different views of the first embodiment of the mount system.
Figure 3B:
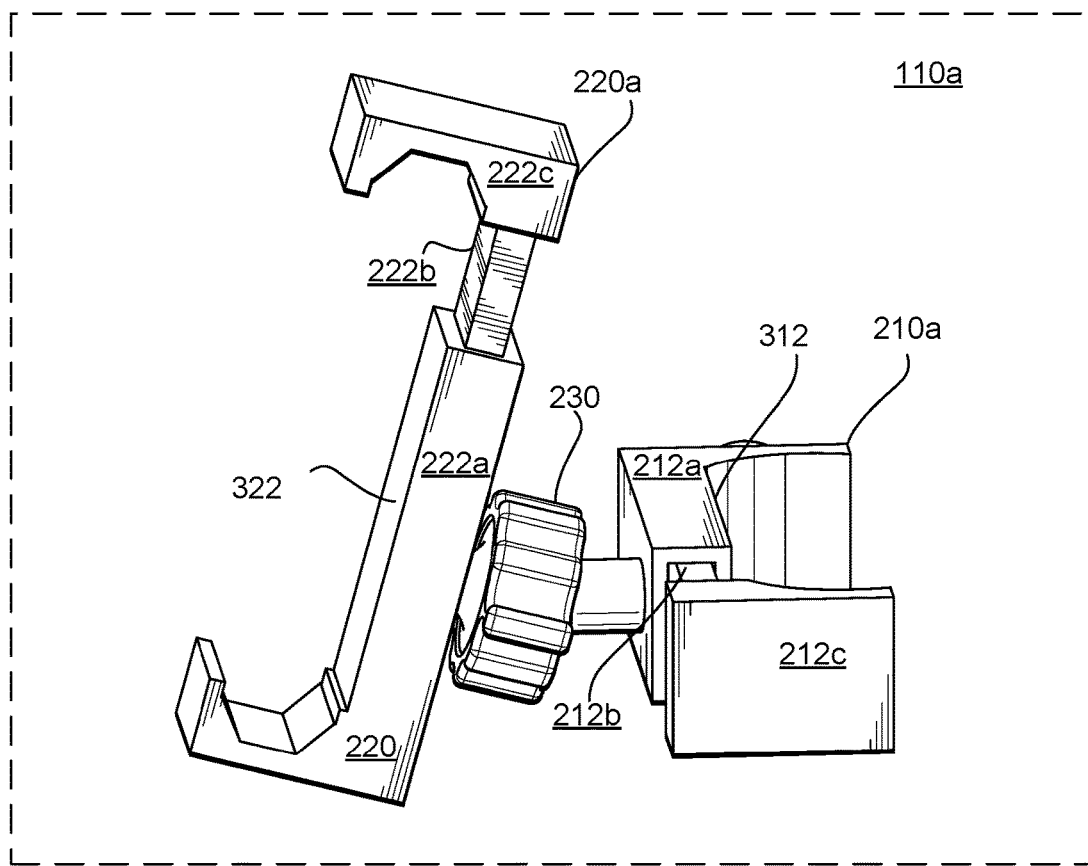
Figure 3C:
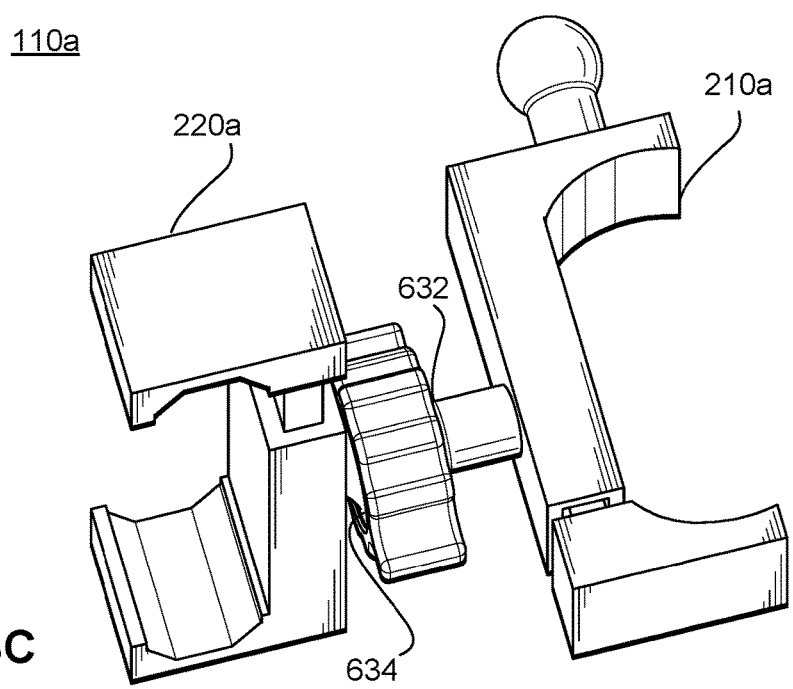

FIGS. 3A-3C illustrate different views of a first embodiment of the mount 110a, in accordance with some embodiments. FIG. 3A provides a perspective view 300 of the first embodiment of the mount 110a. The mount 110 includes a first assembly 210a, a second assembly 220a, and a coupling mechanism 230. In some embodiments, the first embodiment of the mount 110a can be a unitary piece. More specifically, in some embodiments, the first assembly 210a, the second assembly 220a, and the coupling mechanism 230a are a single body that is configured to receive the medical device 150 and the electronic device 170, and is configured to move the devices in unison (e.g., via the single body mount). In some embodiments, the medical device 150 and the electronic device 170 are fixed with respect to one another. Alternatively, in some embodiments, the medical device 150 and the electronic device 170 are adjustable with respect with one another. In some embodiments, the mount 110 can include one or more components (e.g., at least one or more of the first assembly 210a, the second assembly 220a, and the coupling mechanism 230 are individual components configured to be coupled together to form the first embodiment of the mount 110a).

The first assembly 210a is configured to receive a medical device 150. The first assembly 210a includes a first member formed by one or more first member components 212a-212c configured to hold the medical device 130 in a fixed position in relation to a portion of the first member (e.g., first member components 212a or backplate 312). In some embodiments, the dimensions of the first member are adjustable, via adjustments to one or more of the first member components 212a-212c, to at least three different positions (e.g., height, width, depth, etc.) based on dimensions of the medical device 150. In particular, the first member is designed such that its size is adjustable, via the one or more first member components 212a-212c, to receive medical devices 150 of a number of different sizes, orientations (e.g., landscape, portrait, diagonal, and/or other rotations along the x, y and z axis), and/or form factors. In this way, the first embodiments of mount 110a is flexibly able to be used with medical devices 150 made by a number of different manufacturers, many of which vary in their size and shape. Alternatively, in some implementations, a dimension of the first member (e.g., a width (w1) or the distance between first member components 212a and 212c) is adjustable to one of at least three different predefined positions, each of the at least three different predefined positions associated with a respective medical device 150 having at least one dimension (e.g., a width of the medical device 150) that substantially matches a dimension of a respective predefined position of the first member (based on the one or more first member components 212a-212c). In some implementations, one or more dimensions of the first member are adjustable along a sliding scale of values (in other words, the dimension of the first member can be flexibly defined and is not limited to a set of predefined positions). For example, as shown between FIGS. 3A and 3B, the first member component 212c can be separated from (or slide out from) the first member component 212a (revealing the first member component 212b) to adjust the width w1 as desired.

In some embodiments, the dimensions of the first member can be further adjusted using one or more of Velcro, one or more magnets, a clamp, one or more screws, one or more nuts, a slider, and a vise. For example, the first member can be configured to hold the medical device 150 in the fixed position in relation to a portion of the backplate 312 and Velcro can be further wrapped around the medical device 150 and used to secure the medical device 150 to the first member.

In some embodiments, the one or more first member components 212a-212c include a release mechanism 314 configured to release the medical device 150 from being held by the one or more first member components 212a-212c. In some embodiments, the release mechanism 314 includes one or more of a spring-loaded release, detachable surfaces, attachable surfaces (e.g., an interfering surface configured to remove a magnetic force), actuators (e.g., electrical switches, electrical motors, etc.), and/or other similar devices. In some embodiments, in response to receiving an input, the release mechanism 314 releases the medical device 150 (i.e., detaches the medical device 150 from the first assembly 210a (or first member components 212a-212c)). In some embodiments, the input on the release mechanism 314 of the first member components 212a-212c includes one or more of actuating a button, actuating a switch, providing a signal via the electronic device 170, and providing a signal via the medical device 150.

The second assembly 220b is configured to receive an electronic device 170. The second assembly 220b includes a second member formed by one or more second member components 222a-222c configured to hold the electronic device 170 in a fixed position in relation to a portion of the second member. In some embodiments, the dimensions of the second member are adjustable, via adjustments to one or more of the second member components 222a-222c, to at least three different positions (e.g., height, width, depth, etc.) based on dimensions of the electronic device 170. Similar to the first member, the second member is designed such that its size is adjustable to receive electronic devices 170 of a number of different sizes, orientations (e.g., landscape, portrait, diagonal, and/or other rotations along the x, y and z axis), and/or form factors. In this way, the first embodiment of the mount 110a can be used with electronic devices 170 made by a number of different manufacturers, many of which vary in their size and shape. Alternatively, in some implementations, a dimension of the second member (e.g., a width (w2) or the distance between second member components 222a and 222c) is adjustable to one of at least three different predefined positions, each of the at least three different predefined positions associated with a respective electronic device 170 having at least one dimension (e.g., a width of the electronic device 170) that substantially matches a dimension of a respective predefined position of the second member (based on the one or more second member components 222a-222c). In some implementations, one or more dimensions of the second member is adjustable along a sliding scale of values (in other words, the dimension of the second member can be flexibly defined and is not limited to a set of predefined positions similar to the example provided above for the first member).

In some embodiments, the dimensions of the second member are adjustable using one or more of Velcro, one or more magnets, a clamp, one or more screws, one or more nuts, a slider, and a vise. For example, the second member 222 can be designed to hold the electronic device 170 in the fixed position in relation to a portion of the second member via a magnetic force.

In some embodiments, the one or more second member components 222a-222c include a release mechanism 324 configured to release the electronic device 170 from being held by the second member. In some embodiments, the release mechanism 324 includes one or more of a spring-loaded release, detachable surfaces, attachable surfaces (e.g., an interfering surface configured to remove a magnetic force), actuators (e.g., electrical switches, electrical motors, etc.), and/or other similar devices. In some embodiments, in response to receiving an input, the release mechanism 324 releases the electronic device 170 (i.e., detaches the electronic device 170 from the second assembly 220 (or second member 222)). In some embodiments, the input on the release mechanism 324 of the second member 220 includes one or more of actuating a button, actuating a switch, providing a signal via the electronic device 170, and providing a signal via the medical device 150.

In some embodiments, the coupling mechanism 230 is configured to lock the first assembly 210a (or the one or more first member components 212a-212c) and second assembly 220a (or the one or more second member components 222a-212c) in certain positions relative to one another. For example, in some embodiments, the coupling mechanism 230 is an articulating connection between the first assembly 210a and the second assembly 220b. In some embodiments, the coupling mechanism 230 allows for the medical device 150 and the electronic device 170 to be optimally positioned and locked in place for a procedure. Optimally positioned, for purposes of this disclosure, means positioning the medical device 150 such that the medical device 150 collects and provides consistent imaging data (or other data collected by the medical device 150), positioning the medical device 150 such that the medical device 150 has the desired orientation (e.g., oriented to capture landscape and/or portrait image), positioning the medical device 150 such that the medical device 150 does not interfere with one or more medical procedures being performed. Additionally, optimally positioned, for purposes of this disclosure, means positioning the electronic device 170 such that the display 175 is always visible, positioning the electronic device 170 such that the display is angled such the user 130 does not have to reposition their body or portion thereof, and/or positioning the electronic device 170 such that the electronic device 170 does not interfere with one or more medical procedures being performed.

The user 130 can adjust the position of the electronic device 170 relative to the medical device 150 in a number of different angles (e.g., vertical angle 242, horizontal angle 242, and central angles 272 shown in FIGS. 2B and 2C). More specifically, the medical device 150 and the electronic device 170 can be rotated freely around the coupling mechanism 230. Once a user 130 decides on a desired position of the electronic device 170 relative to the medical device 150, the position of the electronic device 170 relative to the medical device 150 can be locked using the coupling mechanism 230. For instance, if the user 130 determines a desired position of the electronic device 170 relative to the medical device 150, the user 130 can engage the lock of the coupling mechanism 230 to fix the desired position. The user 130 can change the respective positions of the medical device 150 and the electronic device 170 by releasing the lock and adjusting the first assembly 210a (or the one or more first member components 212a-212c) and second assembly 220a (or the one or more second member components 222a-212c) as desired.

In some embodiments, the coupling mechanism 230 includes one or more of a screw, nut, clamp, vise, magnet, and metallic plate. In some embodiments, the coupling mechanism 230 is an integral part of the first assembly 210a and/or the second assembly 220a. For example, as discussed in detail below in reference to FIG. 6, the first assembly 210a can include a first coupling mechanism 632 and the second assembly 220a can include a second coupling mechanism 234. In other words, the coupling mechanism 230 can be a first coupling mechanism 632 that is part of the first assembly 210 and a second coupling mechanism 634 that is part of the second assembly 220.

In some embodiments, the coupling mechanism 230 includes a release mechanism 332 configured to release (or decouple) the first assembly 210 (or first member) from the second assembly 220 (or second member). In some embodiments, the release mechanism 332 includes one or more of a spring-loaded release, detachable surfaces, attachable surfaces (e.g., an interfering surface configured to remove a magnetic force), actuators (e.g., electrical switches, electrical motors, etc.), and/or other similar devices. In some embodiments, in response to receiving an input, the release mechanism 332 releases the first assembly 210 (or first member) from the second assembly 220 (or second member). In some embodiments, the input on the release mechanism 332 of the coupling mechanism 230 includes one or more of actuating a button, actuating a switch, providing a signal via the electronic device 170, and providing a signal via the medical device 150.

FIG. 3B illustrates the one or more first member components 212a-212c and the one or more second member components 222a-222c in a partially expanded configuration. In particularly, FIG. 3B shows the one or more first member components 212a-212c of the first assembly 210a and the one or more second member components 222a-222c of the second assembly 220b adjusted to fit the respective sizes of the medical device 150 and the electronic device 170. Additionally, the one or more first member components 212a-212c of the first assembly 210a and the one or more second member components 222a-222c of the second assembly 220b can be compressed (or squeezed) to hold the medical device 150 and electronic device 170, respectively. More specifically, one or more first member components 212a-212c and the one or more second member components 222a-222c can be fitted to accommodate the size of the medical device 150 and/or electronic device 170. In some embodiments, a surface of the medical device 150 and the electronic device 170 is mated with a backplate 312 and 322, respectively. The surface of the medical device 150 can be any side of the medical device 150. The surface of the electronic device 170 can be any side of the electronic device 170 other than the side include the display 175. In some embodiments, the backplate 312 and 322 is magnetized such that the medical device 150 and/or the electronic device 170 can be easily attached and detached from the first embodiment of the mount 110a.

FIG. 3C illustrates a top view of the mount 110, in accordance with some embodiments. FIG. 3C show that the first coupling mechanism 632 that is part of the first assembly 210a can be a male connector and the second coupling mechanism 634 that is part of the second assembly 220a can be a female connector, the first coupling mechanism 632 and the second coupling mechanism 634 coming together (and being locked in place) to form the first embodiment of the mount 110a.

Figure 4:
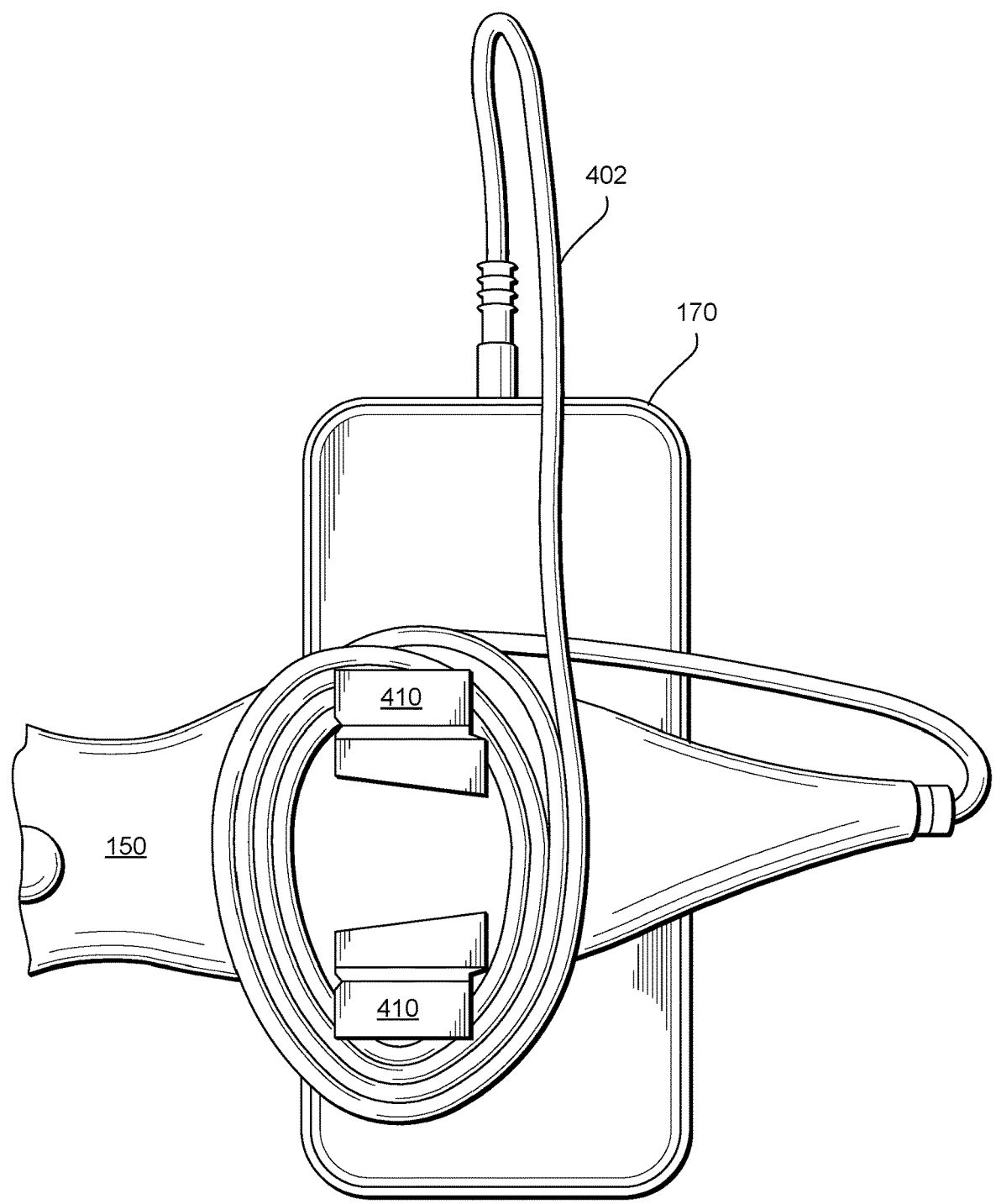
FIG. 4 illustrate a cable-management component that can be added to the first, second, and/or third embodiments of the mount system.

FIG. 4 illustrates a cable-management component 410 that can be added to the first, second, and/or third embodiments of the mount system. In some embodiments, the first, second, and/or third embodiments of the mount 110a-110c include a cable-management component 410 configured to hold a cable 402 that communicatively connects the medical device 150 to the electronic device 170 (FIG. 1) to enable the medical device to provide its imaging data to the electronic device. The cable 402 is configured to convey the imaging data from the medical device 150 to the electronic device 170. In some embodiments, the cable is configured to provide power from the medical device 150 to the electronic device 170, and vice versa.

The cable-management component 410 can include forks or hooks that are configured to have excess cable 402 of the medical device 150 wrapped around them. In some embodiments, the cable-management component 410 is configured to rotate (e.g., via user rotation or a motor) such that the excess cable 402 is quickly wrapped or unwrapped from the cable-management component 410. In some embodiments, the medical device 150 conveys the imaging data wirelessly to the electronic device 170. In these embodiments, no cable-management system need be included with the first, second, and/or third embodiments of the mount 110a-110c.

Figure 5A:
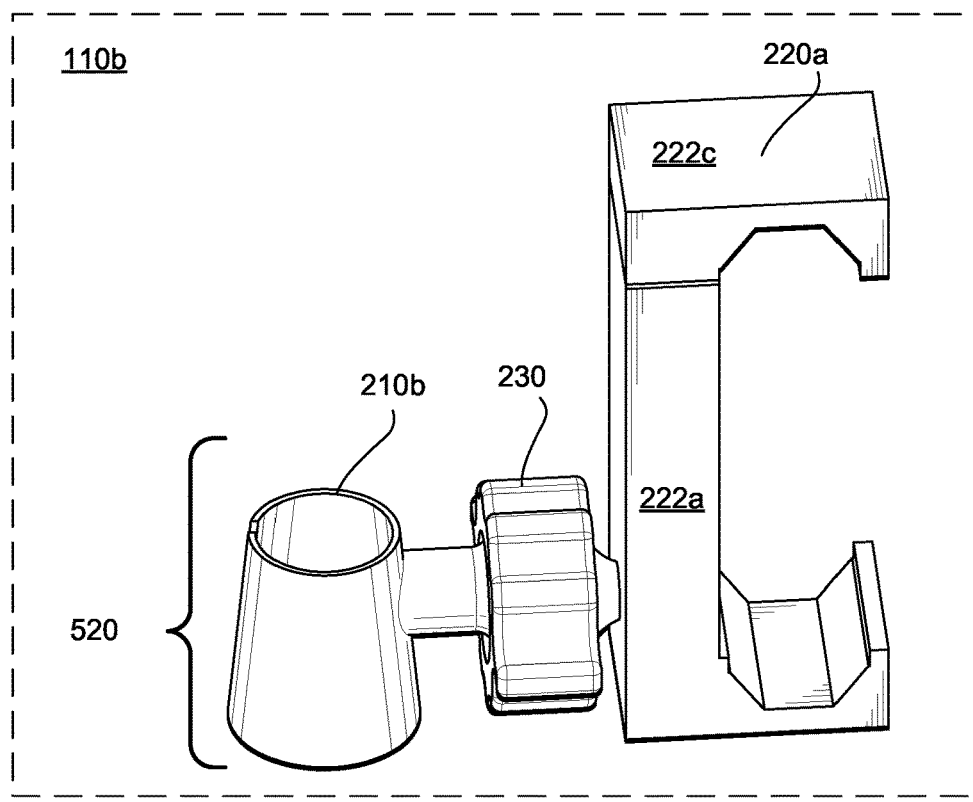
FIGS. 5A-5D illustrate different views of the second embodiment of the mount system.
Figure 5B:
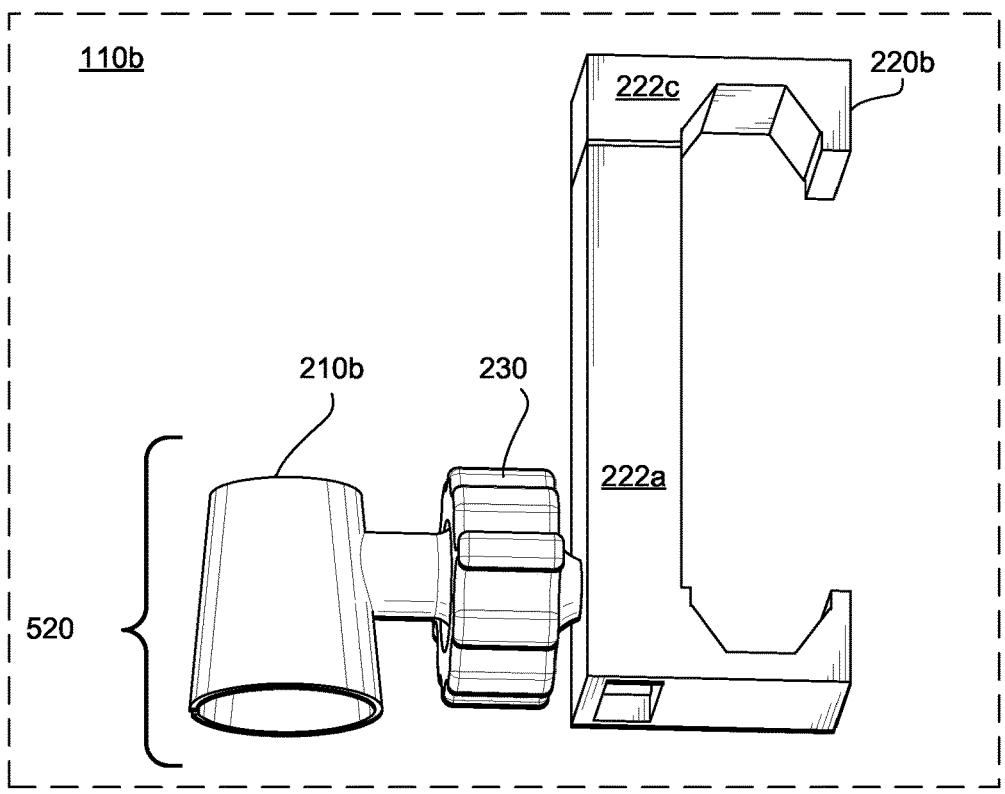

FIGS. 5A-5B illustrate different views of the second embodiment of the mount. The second embodiment of the mount 110b includes a different first assembly 210b including an alternate first member, such as an adjustable frame 520. The adjustable frame includes predetermined dimensions that are less than dimension of the medical device 150. The adjustable frame 520, when receiving the medical device 150, expands to accommodate the size of the medical device 150. In some embodiments, the adjustable frame 520 is substantially rigid such that it does not expand to a size larger than the medical device 150.

Figure 5C:
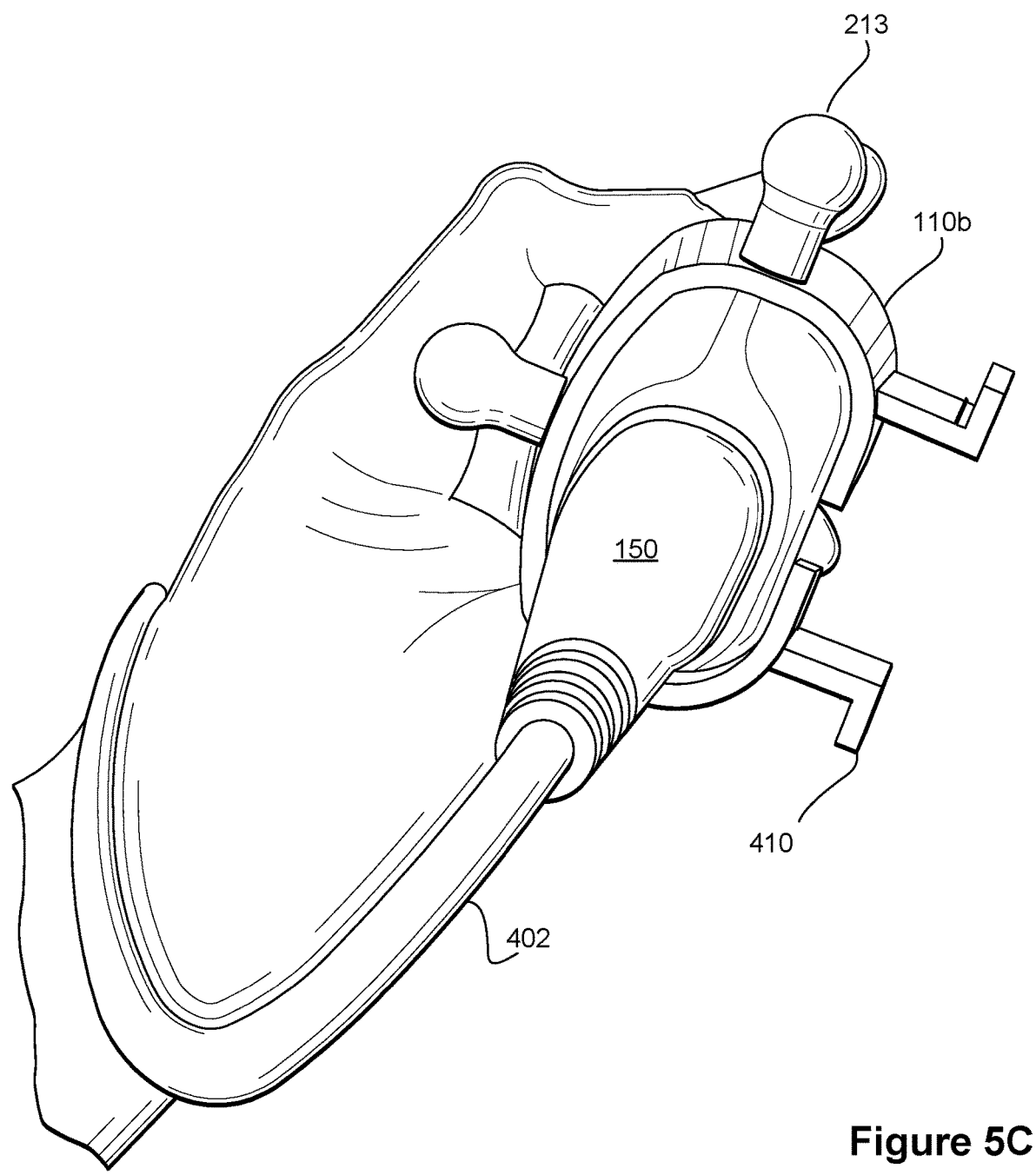
Figure 5D:
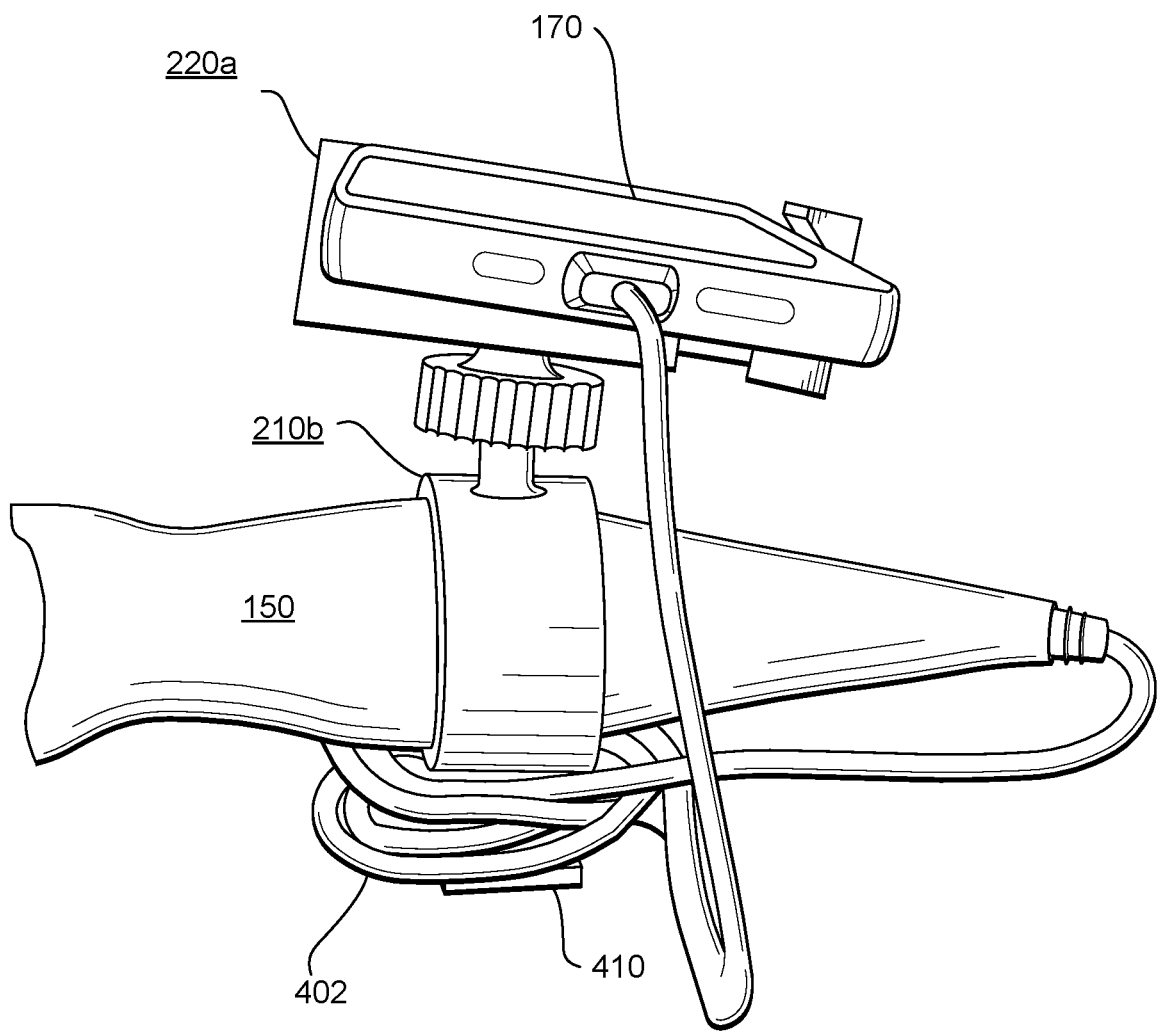

FIGS. 5B-5D illustrate the second embodiment of the mount 110b with the cable-management component 410 (FIG. 4). In some embodiments, the second embodiment of the mount 110b includes the cable-management component 410 in order to hold a cable 402 that communicatively connects the medical device 150 to the electronic device 170 (FIG. 1) to enable the medical device to provide its imaging data to the electronic device. The cable 402 is configured to convey the imaging data from the medical device 150 to the electronic device 170. In some embodiments, the cable is configured to provide power from the medical device 150 to the electronic device 170, and vice versa. Additional information on the cable-management component 410 is provided above in FIG. 4.

Figure 6:
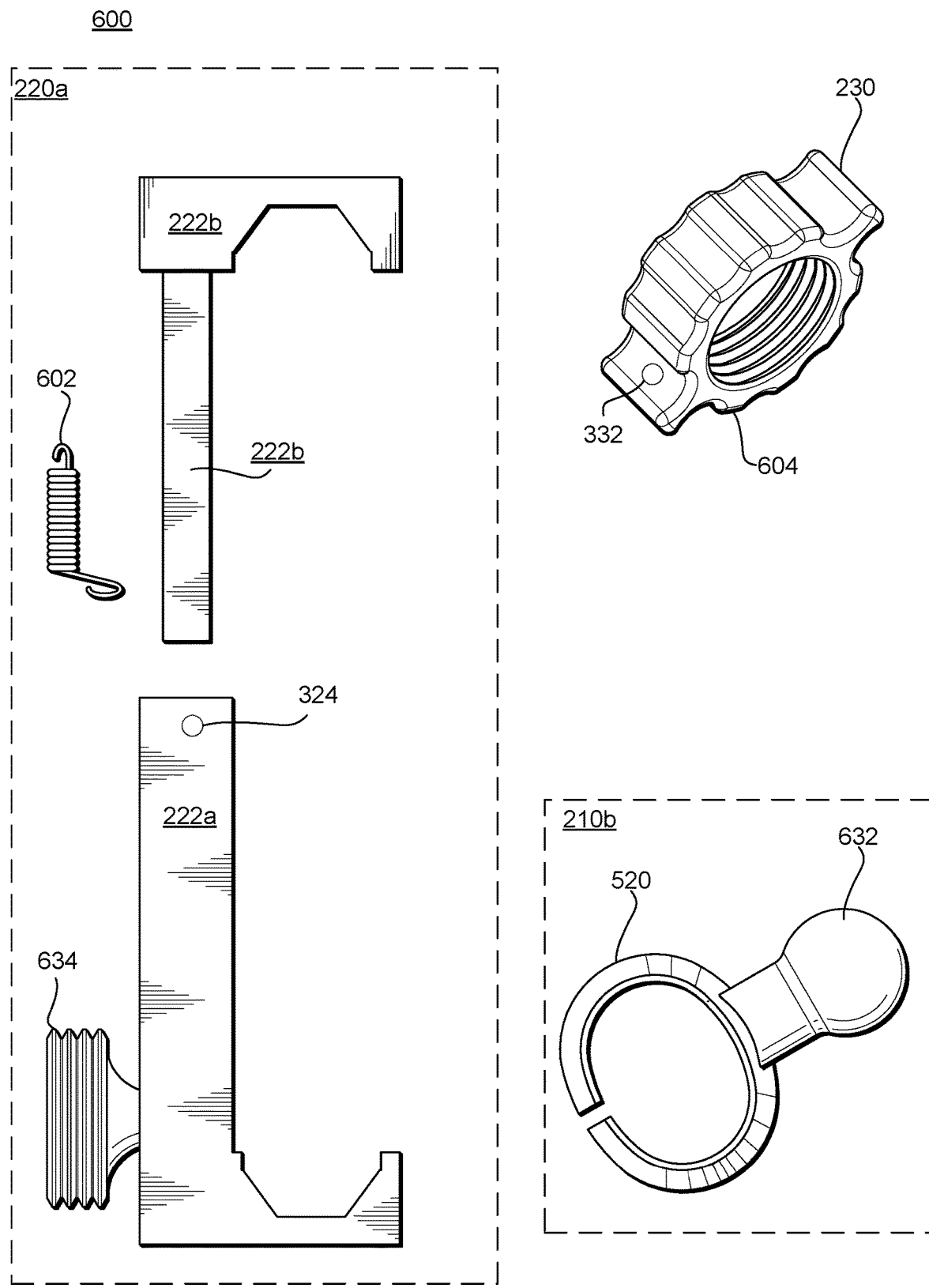
FIG. 6 illustrates a deconstructed (or exploded) view of the second embodiment of a mount system.

FIG. 6 illustrates a deconstructed (or exploded) view 500 of the second embodiment of the mount 110b. Deconstructed view 600 shows the different first assembly 210b, the second assembly 220a, and the coupling mechanism 230 of the second embodiment of the mount 110b. The different components in deconstructed view 500 are combined to form the second embodiment of the mount 110b.

Deconstructed view 600 illustrates the different first assembly 210b with an adjustable frame 520 illustrated in FIGS. 5A-5D. As described above, the adjustable frame 520 includes predetermined dimensions that are less than dimension of the medical device 150. When a medical device 150 (FIG. 1) is placed in the adjustable frame 520 is expands to fit the size of the medical device 150. Deconstructed view 600 further shows the second assembly 220a including one or more second member components 222a-222c illustrated in FIGS. 3A-3C. Further, the second assembly 210a includes a release mechanism 324 to quickly release the electronic device 170. The release mechanism 324 can be spring-loaded release (e.g., the shown spring 602 being part of the release mechanism 324).

Deconstructed view 600 further shows the coupling mechanism 230. In some embodiments, the coupling mechanism is formed of one or more components. Similar to the first embodiment of the mount 110a, the coupling mechanism 230 can be an integral part of the second embodiment of the mount 110b. For example, the coupling mechanism 230 be a first coupling mechanism 632 (e.g., a male connector formed on the different first assembly 210b), a second coupling mechanism 634 (e.g., a female connector formed on the second assembly 220a). In some embodiments, the coupling mechanism 230 is a component that joints the different first assembly 210b and the second assembly 220a. For example, the coupling mechanism 230 can be a locking component 604 (e.g., nut) that connects the different first assembly 210b and the second assembly 220a. In particular, the second coupling mechanism 634 is configured to receive the first coupling mechanism 632, and the locking component 604 is configured to lock the different first assembly 210b and second assembly 220a in a desired position relative to one another. In some embodiments, the first coupling mechanism 632 and the second coupling mechanism 234 include one or more of a male connector, female connector, magnet, vice, clamp, and screw.

FIGS. 7A-7C are flow diagrams showing a method of performing medical procedures concurrently, in accordance with some embodiments. Operations (e.g., steps) of the method 700 may be performed using a first, second, or third embodiment of the mount 110a-110c (FIGS. 1A-6 and FIGS. 9A1-9C). In some embodiments, some, but not all, of the operations illustrated in FIGS. 7A-7C, are performed. Similarly, one or more operations illustrated in FIGS. 7A-7C may be optional (identified by dotted lines) or performed in a different sequence. Furthermore, two or more operations of FIGS. 7A-7C consistent with the present disclosure may be overlapping in time, or almost simultaneously.

The method 700 includes performing (702) a first medical procedure with one hand, the first medical procedure includes operating (704) a first, second, or third embodiment of the mount 110a-110c (FIG. 1A-1B) configured to enable one-handed control of both a medical device 150 and a handheld electronic device (e.g., electronic device 170). For ease of reference, the first, second, or third embodiments of the mount 110a-110c will be referred to as "the mount 110." The mount 110 is configured to hold the medical device 150 and the handheld electronic device 170, and configured to allow for one-handed movement of the medical device 150 and the electronic device 170 in unison.

The mount 110 includes (706) a first assembly 210a-210c configured to receive the medical device 150. The medical device 150 is configured to provide imaging data of a patient 160 to the handheld electronic device 170 having a display 175. The first assembly 210a-210c including a first member (e.g., one or more first member components 212a-212c or adjustable frame 520) configured to hold the medical device 150 in a fixed position in relation to a portion of the first member 212 (e.g., backplate 312). Optionally, the mount 110 includes (708) a second assembly 220a-220b configured to receive the electronic device 170. The electronic device 170 is configured to display the imaging data of the patient 160 received from the medical device 150. The second assembly 220a-220b includes a second member (e.g., one or more second member components 222a-222c) configured to hold the electronic device 170 in a fixed position in relation to a portion of the second member 222. In some embodiments, the electronic device 170 is positioned (710) above the medical device 150 such that an operator (e.g., a user 130) of the mount 110 is able to continue viewing the imaging data of the patient 160 on the display 175 of the electronic device 170 during the one-handed movement. For example, as illustrated in FIGS. 1A-2C, the electronic device 170 is positioned above a probe portion of the medical device 150 (e.g., bottom portion of the ultrasound probe). The mount 110 includes (712) a coupling mechanism 230 configured to couple the first assembly 210a-210c to the second assembly 220a-220b such that the first assembly 210a-210c and the second assembly 220-220b are movable relative to one another.

In some embodiments, operating the mount 110 to perform the first medical procedure includes (714) moving and/or holding the medical device 150 and the electronic device 170 together in one hand while using the other hand opposite the one hand to ergonomically perform the second medical procedure. In some embodiments, when the first member (e.g., the one or more first member components 212a-212c or the adjustable frame 520) is holding the medical device 150 and the second member (e.g., the one or more second member components 222a-222c) is holding the electronic device 170, operating the mount 110 to perform the first medical procedure includes (716) holding and moving the medical device 150 to enable the one-handed movement of the medical device 150 and the electronic device 170 in unison.

In some embodiments, while performing the first medical procedure with one hand, the method 700 includes (718-a) adjusting a position of one or more of the medical device 150 and the electronic device 170. Adjusting the position of the one or more of the medical device 150 and the electronic device 170 includes, at the mount 110, one or more of adjusting (718-b) the medical device 150 in the first member, adjusting (718-c) the electronic device 170 in the second member, adjusting (718-d) the first assembly 210a-210c relative to one or more of the second assembly 220a-220b and the coupling mechanism 230, adjusting (718-e) the second assembly 220a-220b relative to one or more of the first assembly 210a-210c and the coupling mechanism 230, and securing (718-f), via the coupling mechanism 230, an adjusted position of one or more of the first assembly 210a-210c, the first member, the second assembly 220a-220b, and the second member. In particular, the mount 110 allows user 130 to change the position of the medical device 150 and the electronic device 170 as desired as described above in reference to FIGS. 2A-2C and 3A.

In some embodiments, a dimension of the first member is adjustable (720) to one of at least three different predefined positions. Each of the at least three different predefined positions associated with a respective medical device 150 having at least one dimension that substantially matches a dimension of a respective predefined position of the first member. Alternatively, in some embodiments, dimensions of the first member are adjustable to at least three different positions based on dimensions of the medical device 150. In some embodiments, the dimension of the first member is adjustable (722) using one or more of an adjustable body, Velcro, one or more magnets, a clamp, a slider, and a vise. In some embodiments, a dimension of the second member is adjustable (724) to one of at least three different predefined positions based on dimensions of the electronic device 170. Each of the at least three different predefined positions associated with a respective electronic device 170 having at least one dimension that substantially matches a dimension of a respective predefined position of the second member. Alternatively, in some embodiments, dimensions of the second member are adjustable to at least three different positions based on dimensions of the electronic device 170. In some embodiments, the dimension of the second member is adjustable (726) using one or more of an adjustable body, Velcro, one or more magnets, a clamp, a slider, and a vise.

The method 700 includes performing (728) a second medical procedure with another hand opposite the one hand. The second medical procedure is performed concurrently with the first medical procedure. In some embodiments, the method 700 includes performing (730) the second medical procedure includes utilizing the imaging data of the patient 160 displayed by the handheld electronic device 170 to complete the procedure. For example, the mount 110 may hold an ultrasound probe and a smartphone together such that the user 130 has one-handed control of both the ultrasound probe and the smartphone to view imaging data of a patient 160 while leaving the user's 130 other hand free to perform an second medical procedure, such as peripheral IVs, central lines, nerve blocks, etc.

In some embodiments, the first member and second member include (732-*a*) a respective release mechanism (e.g., 314 and 324, respectively), and the method 700 further includes receiving (732-*b*) an input at the respective release mechanism to release one or more of the medical device 150 and/or the electronic device 170 from being held by the respective member, and, in response to receiving the input, releasing one or more of the medical device 150 and the electronic device 170. In some embodiments, the input includes (734) one or more of actuating a button on the respective member, actuating a switch, providing a signal via the electronic device 170, and providing a signal via the medical device 150. In some embodiments, the respective release mechanisms include (736) one or more of a spring-loaded release, detachable surfaces, attachable surfaces, and actuators.

In some embodiments, before performing the first medical procedure with one hand, at the mount 110 providing (738-*a*) the medical device 150 to the first assembly 210*a*-210*c*, securing (738-*b*) the medical device 150 to the first assembly 210*a*-210*c*, providing (738-*c*) the electronic device 170 to the second assembly 220*a*-220*b*, securing (738-*d*) the electronic device 170 to the second assembly 220*a*-220*b*, and securing (738-*e*) the coupling mechanism 302 such that the first member and the second member have a fixed position relative to one another.

FIGS. 8A and 8B are flow diagram showing a method of forming a mount 110, in accordance with some embodiments. In some embodiments, some, but not all, of the operations illustrated in FIG. 8A, are performed. Similarly, one or more operations illustrated in FIG. 8A may be optional (identified by dotted lines) or performed in a different sequence. Furthermore, two or more operations of FIG. 8A consistent with the present disclosure may be overlapping in time, or almost simultaneously.

In FIG. 8A, a method 800 forming a first, second, and third embodiment of a mount 110*a*-110*c* (FIG. 1A-1B) includes forming (802) a first assembly 210*a*-210*c* configured to receive the medical device 150. The medical device 150 is configured to provide imaging data of a patient 160 to the handheld electronic device 170 having a display 175. The first assembly 210 includes a first member (e.g., one or more first member components 212*a*-212*c* or an adjustable frame 520) configured to hold the medical device 150 in a fixed position in relation to a portion of the first member. In some embodiments, the method 800 includes forming (804) one or more of an adjustable body, Velcro, one or more magnets, a clamp, a slider, and a vise operable with the first member such that dimensions of the first member are adjustable to at least three different positions based on dimensions of the medical device 150. In some embodiments, the method 800 includes forming (806) a release mechanism 314 operable with the first member. The release mechanism 314 is configured to release the medical device 150 from being held by the first member.

The method 800 includes forming (808) a second assembly 220*a*-220*b* configured to receive the electronic device 170. The electronic device 170 configured to display the imaging data of the patient 160 received from the medical device 150. The second assembly 220*a*-220*b* includes a second member (e.g., one or more second member components 222*a*-222*c*) configured to hold the electronic device 170 in a fixed position in relation to a portion of the second member. In some embodiments, the method 800 includes forming (810) one or more of an adjustable body, Velcro, one or more magnets, a clamp, a slider, and a vise operable with the second member such that dimensions of the second member are adjustable to at least three different positions based on dimensions of the electronic device 170. In some embodiments, the method 800 further includes forming (812) a release mechanism 324 operable with the second member. The release mechanism 324 is configured to release the electronic device 170 from being held by the second member 222.

The method 800 further includes forming (814) a coupling mechanism 230 configured to couple the first member to the second member such that the first member and the second member are movable relative to one another. In some embodiments, forming (816) the coupling mechanism 230 includes including one or more of a screw, a nut, a clamp, a vise, a magnet, and a metallic plate in the coupling mechanism 230. In some embodiments, forming (818) the coupling mechanism 230 includes forming a first coupling mechanism 632 that is part of the first assembly 210*a*-210*b* and a second coupling mechanism 634 that is part of the second assembly 220*a*. The first coupling mechanism 632 and the second coupling mechanism 634 include one or more of a male connector, a female connector, a magnet, a vice, a clamp, and a screw. Examples of the first coupling mechanism 632 and the second coupling mechanism 634 are provided above in reference to FIGS. 2B-3C and 5A-6. In some embodiments, forming the coupling mechanism 230 includes forming a magnetic coupling mechanisms 932 that is part of the first assembly 210*c* and a magnetic coupling mechanisms 934 that is part of the second assembly 220*b*. Additional detail on the magnetic coupling mechanisms 932 and 934 are provided below in reference to FIGS. 9A1-9C. In some embodiments, the method 800 includes forming (820) a release mechanism 332 operable with the coupling mechanism 230. The release mechanism 332 is configured to release the first assembly 210*a*-210*c* and the second assembly 220*a*-220*b* from being coupled together.

The first member holds the medical device 150 and the second member 222 holds the electronic device 170 such that the mount 110 is configured (822) to allow for one-handed movement of the medical device 150 and the electronic device 170 in unison. In some embodiments, the first assembly 210*a*-210*c* (or first member), the second assembly 220*a*-220*b* (or second member), and the coupling mechanism 230 are formed (824) as a unitary piece. In some embodiments, the first assembly 210*a*-210*c* (or first member), the second assembly 220a-220b (or second member), and the coupling mechanism 230 are formed (826) as individual components.

FIGS. 9A1-9C illustrate a third embodiment of a mount system 100c. FIG. 9A1 illustrates another first assembly 210c for a third embodiment of a mount 110c. The other first assembly 210c is similar to the embodiments described above in reference to FIGS. 1A-6. For example, the first assembly 210c includes a first member configured to receive a medical device 150 similar to the adjustable frame 520 described above in FIGS. 5A-6. Additionally, the other first assembly 210c includes an integrated coupling mechanism 230. More specifically, the other first assembly 210c includes at least two magnetic coupling mechanisms 932a and 932b. The magnetic coupling mechanisms 932a and 932b (and the other magnetic coupling mechanisms described herein) can be configured as MagSafe-compatible (MagSafe is a trademark of Apple, Inc. of Cupertino, CA) components/accessories, such that for embodiments in which MagSafe-compatible magnetic coupling mechanisms are utilized, the magnetic coupling mechanisms can be configured to both magnetically hold and also deliver a sufficient charge to a connected smartphone device.

Each of the at least two magnetic coupling mechanisms 932a and 932b of the other first assembly 210c is configured to magnetically couple to at least one magnetic coupling mechanisms 934 of another second assembly 220b (described below in reference to FIG. 9A2) such that the other first assembly 210c and the other second assembly 220b couple together. The at least two magnetic coupling mechanisms 932a and 932b of the other first assembly 210c are positioned at 90 degrees from one another. This configuration allows the other first assembly 210c and the other second assembly 220b to easily switch between "in-plane" and "out of plane" configurations as described below.

FIG. 9A2 illustrates the other second assembly 220b for the third embodiment of a mount 110c. The other second assembly 220b is similar to the embodiments described above in reference to FIGS. 1A-6. For example, the other second assembly 210b includes one or more second member components 222a-222c configured to receive and electronic device 170 similar to those described above in FIGS. 1A-6. Additionally, the other second assembly 220b includes an integrated coupling mechanism 230. More specifically, the other second assembly 220b includes at least one magnetic coupling mechanisms 934. As described above in reference to FIG. 9A1, the at least one magnetic coupling mechanisms 934 of the other second assembly 220b is configured to magnetically couple to each of the at least two magnetic coupling mechanisms 932a and 932b of the other first assembly 210c.

Figure 9B:
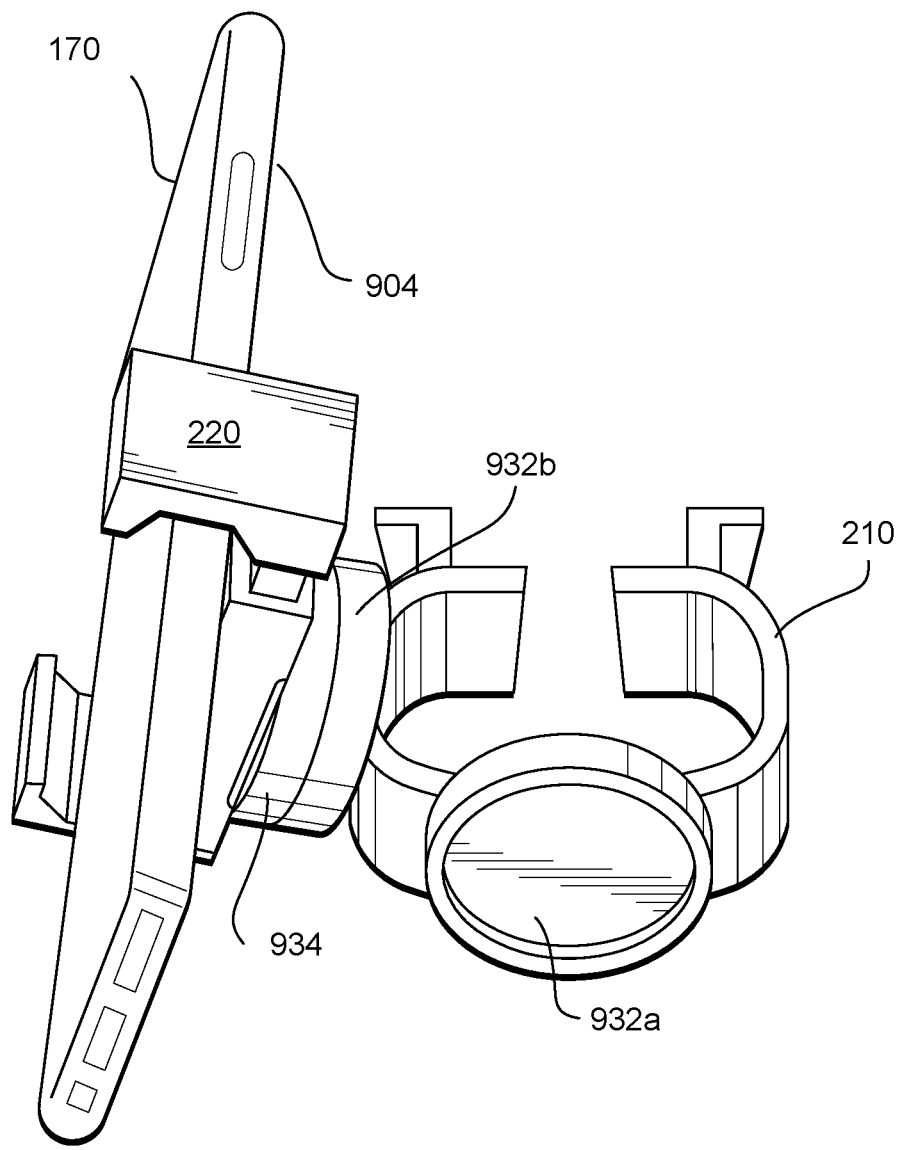

FIG. 9B illustrates the third embodiment of a mount 110c with the other first assembly 210c and the other second assembly 220b in an "in-plane" configuration. An "in-plane" configuration, as shown in FIG. 9B, has a first surface 902 (shown in FIG. 9A1) of the medical device 150 perpendicular to a first surface 904 (shown in FIG. 9A2) of the electronic device 170. When a magnetic coupling mechanisms 932a or 932b of the first assembly 210c is magnetically coupled to the at least one magnetic coupling mechanisms 934 of the second assembly 220, their respective positions are fixed with one another. Although the respective positions of the magnetic coupling mechanisms 932a (or 932b) and the at least one magnetic coupling mechanisms 934 are fixed with one another, the first assembly 210c and the second assembly 210b may allow for the position of the medical device 150 and the electronic device 170 to be to be adjusted relative to one another. For example, the medical device 150 and the electronic device 170 may be adjusted between portrait or landscape orientations. Additional examples of adjustments to relative positions of the medical device 150 and the electronic device 170 are described above in reference to FIGS. 2A-2C.

The at least two magnetic coupling mechanisms 932a and 932b of the other first assembly 210c and the at least one magnetic coupling mechanisms 934 of another second assembly 220b can be configured to operate as a charging surface. More specifically, the magnetic coupling mechanisms 932a or 932b of the other first assembly 210c when magnetically coupled to the at least one magnetic coupling mechanisms 934 of the other second assembly 220b can be used to transfer power from the electronic device 170 to the medical device 150, and vice versa. The transferred power can be used to power and/or charge the electronic device 170 and/or the medical device 150. Alternatively or additionally, a magnetic coupling mechanisms 932a and/or 932b of the other first assembly 210c and/or the at least one magnetic coupling mechanisms 934 of the other second assembly 220b can include a power source (e.g., a battery) and/or be coupled to a power source (e.g., an outlet), and transfer power to the electronic device 170 and/or medical device 150.

As described above, the at least two magnetic coupling mechanisms 932a and 932b of the other first assembly 210c allow for other first assembly 210c and the other second assembly 220c to be easily be positioned in "in-plane" and "out of plane" configurations.

Figure 9C:
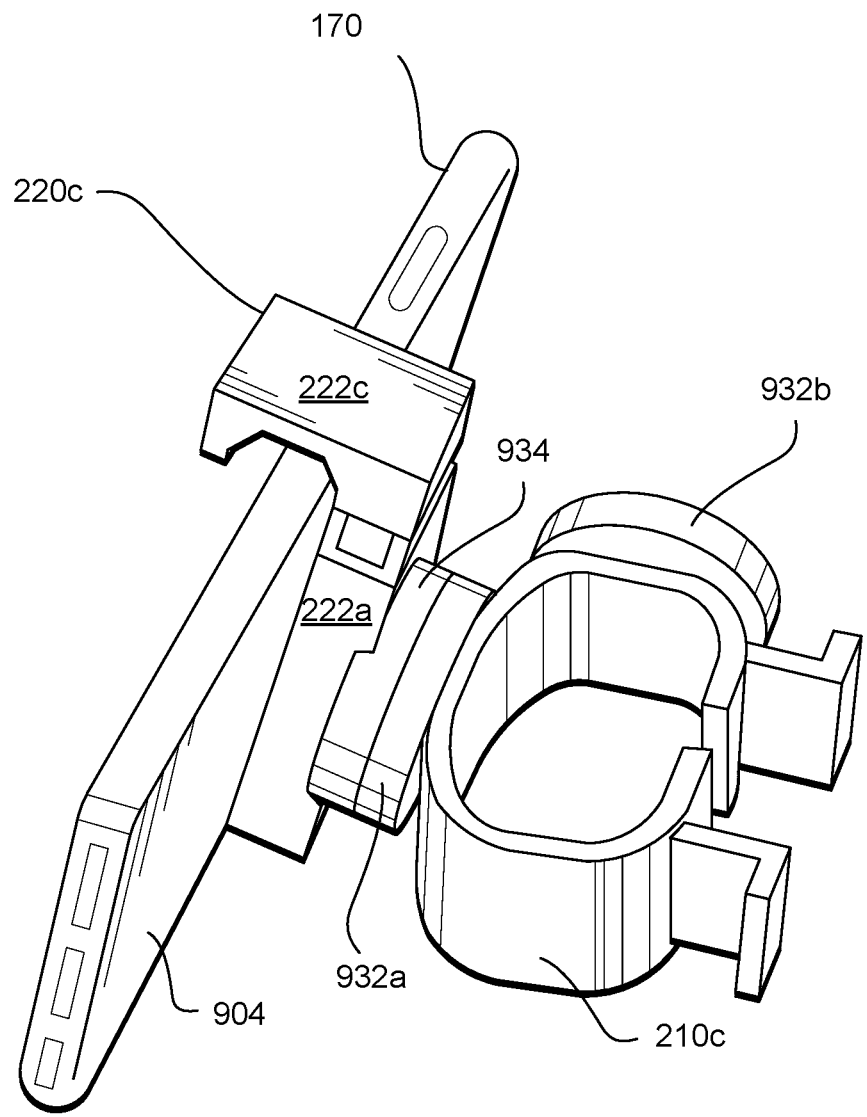

For example, as shown between FIGS. 9B and 9C, a user 130 can couple the other first assembly 210c and the other second assembly 220b via the a first magnetic coupling mechanisms 932b and the magnetic coupling mechanisms 934 to configure the third embodiment of the mount 110c in an "in-plane" configuration, and then couple the other first assembly 210c and the other second assembly 220b via a second magnetic coupling mechanisms 932c and the magnetic coupling mechanisms 934 to configure the third embodiment of the mount 110c in an "out of plane" configuration.

FIG. 9C illustrates the third embodiment of the mount 100c with an "out-of-plane" configuration. An "out-of-plane" configuration, as shown in FIG. 9C, has the first surface 902 of the medical device 150 parallel with the first surface 904 of the electronic device 170. The "in-plane" and "out-of-plane" configurations allow the user 130 greater flexibility in moving the medical device 150 to different positions without interfering with a procedure. The "in-plane" and "out-of-plane" configurations further allow the user to reach one or more positions on a patient's body that would normally be difficult to reach and generate the desired imaging data.

While the "in-plane" and "out-of-plane" configurations are discussed above with reference to the third embodiment of the mount 110c, the skilled artisan in this field will appreciate upon reading this disclosure that that the "in-plane" and "out-of-plane" configurations can be achieved using a single coupling mechanism 230, a single first coupling mechanism 632, and/or a single second coupling mechanism 634, such as those described above in reference to FIGS. 3A-3B and FIGS. 5A-6. For example, the coupling mechanism 230 can be a joint that allows for adjustments of at least 90 degrees.

While three primary embodiments of a mount system are discussed here as illustrative examples (e.g., the first embodiment of FIGS. 1A and 2A-4, the second embodiment of FIGS. 1A and 5A-6, and the third embodiment of FIGS. 1B and 9A1-9C), a skilled artisan in this field upon reading this disclosure will understand that other embodiments are also within the scope of this disclosure. As one example, a fourth embodiment of the mount can include integrating a magnet directly into a housing of the medical device 150 (e.g., an ultrasound probe), which can then allow for magnetically connecting a smartphone with an included magnet directly to the medical device 150 without requiring use of either the first 210a-210c or second assemblies 220a-220c described herein. As another example, the third embodiment can also be used in conjunction with the second assembly 220b of the third embodiment of the mount 110c (e.g., second assembly 220b, FIG. 9A2) to allow smartphones without an included magnet to be used with the inventive mount systems described herein. Other changes and configurations are also within the scope of this disclosure, including the use of Velcro, a clamp, a slider, and a vise to couple the medical device 150, electronic device 170, the first assembly 210a-210c, and/or the second assembly 220a-220c.

It will be understood that, although the terms "first," "second," etc. may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

What is claimed is:

1. A mount for enabling one-handed control of both an ultrasound device and an electronic device, the mount comprising:

a first assembly configured to receive an ultrasound device, the ultrasound device configured to be electronically coupled to an electronic device to provide imaging data of a patient to the electronic device having a display, the first assembly including:
a first member configured to hold the ultrasound device;
a second assembly configured to receive the electronic device, the electronic device configured to display the imaging data of the patient received from the ultrasound device, the second assembly including:
a second member configured to hold the electronic device via only a magnetic force in an in-plane configuration with respect to the ultrasound device at a first point in time and an out-of-plane configuration with respect to the ultrasound device at a second point in time that is distinct from the first point in time, the in-plane configuration being distinct from the out-of-plane configuration;
a coupling mechanism configured to couple the first member to the second member such that the first and second members are configured to be movable relative to one another to adjust at least one angle of the electronic device relative to the ultrasound device while the electronic device is positioned in the in-plane configuration with respect to the medical ultrasound device at the first point in time and while the electronic device is positioned in the out-of-plane configuration, distinct from the in-plane configuration, with respect to the medical ultrasound device at the second point in time;
a release mechanism for releasing the first assembly from being coupled with the second assembly, wherein the release mechanism comprises a switch; and
a locking component configured to lock the first member and the second member in a position relative to one another,
wherein:
when the first member is holding the ultrasound device and the second member is holding the electronic device via the magnetic force, the mount is configured to allow for one-handed movement of the ultrasound device and the electronic device in unison, and
when the first assembly is released from being coupled with the second assembly via the release mechanism, the first assembly continues to receive the ultrasound device, the second assembly continues to receive and hold by way of only the magnetic force the electronic device, and the ultrasound device and the electronic device remain electronically coupled; and
the first member includes: (i) an opening for receiving the ultrasound device and (ii) a slot that is separate from the opening, wherein:
the mount includes a cable-management component configured to hold a cable that communicatively and electronically connects the ultrasound device to the electronic device to enable the ultrasound device to provide the imaging data to the electronic device, and
the slot that is separate from the opening is configured such that the cable that communicatively and electronically couples the ultrasound device to the electronic device passes through the slot when the cable is electronically connecting the ultrasound device to the electronic device.

2. The mount of claim 1, wherein, by allowing for one-handed movement of the ultrasound device and the electronic device in unison, an operator of the mount is able to move or hold the ultrasound device and the electronic device together in one hand while using the operator's other hand to ergonomically perform an ultrasound procedure.

3. The mount of claim 2, wherein when the first member is holding the ultrasound device and the second member is holding the electronic device, the mount is configured to allow an operator to hold and move the ultrasound device to enable the one-handed movement of the ultrasound device and the electronic device in unison.

4. The mount of claim 3, wherein, during the one-handed movement of the ultrasound device and the electronic device, the mount is configured to position the electronic device above the ultrasound device such that an operator of the mount is able to continue viewing the imaging data of the patient on the display of the electronic device during the one-handed movement.

5. The mount of claim 4, wherein the ultrasound device is an ultrasound probe.

6. The mount of claim 1, wherein a dimension of the first member is adjustable to one of at least three different predefined positions, each of the at least three different predefined positions associated with a respective ultrasound device having at least one dimension that substantially matches a dimension of a respective predefined position of the first member.

7. The mount of claim 6, wherein the dimension of the first member is adjustable using one or more of an adjustable body, hook-and-loop fastener, one or more magnets, a clamp, a slider, and a vise.

8. The mount of claim 1, wherein
the cable-management component does not include threads.

9. The mount of claim 1, wherein the electronic device is a smartphone or a tablet.

10. The mount of claim 9, wherein a dimension of the second member is adjustable to one of at least three different predefined positions based on dimensions of the electronic device, each of the at least three different predefined positions associated with a respective electronic device having at least one dimension that substantially matches a dimension of a respective predefined position of the second member.

11. The mount of claim 9, wherein, when the electronic device is magnetically coupled to the second member, the electronic device is configured to receive power from a power source.

12. The mount of claim 1, wherein:
when the electronic device is held by the second member in the in-plane configuration with respect to the ultrasound device, a first surface of the ultrasound device is substantially perpendicular to a first surface of the electronic device, and
when the electronic device is held by the second member in the out-of-plane configuration with respect to the ultrasound device, the first surface of the ultrasound device is substantially parallel to the first surface of the electronic device.

13. The mount of claim 12, wherein the electronic device is moved between the in-plane configuration with respect to the ultrasound device and to the out-of-plane configuration with respect to the ultrasound device by adjusting a position of the electronic device using the coupling mechanism.

14. A method of performing ultrasound procedures concurrently, the method comprising:
performing a first ultrasound procedure with one hand of an operator, wherein performing the first ultrasound procedure includes:
operating a mount configured to enable one-handed control of both an ultrasound device and an electronic device, the mount holding the ultrasound device and the electronic device, and configured to allow for one-handed movement of the ultrasound device and the electronic device in unison, the mount including:
a first assembly configured to receive the ultrasound device, the ultrasound device configured to be electronically coupled to the electronic device to provide imaging data of a patient to the electronic device having a display, the first assembly including a first member configured to hold the ultrasound device,
a second assembly configured to receive the electronic device, the electronic device configured to display the imaging data of the patient received from the ultrasound device, the second assembly including a second member configured to hold the electronic device via only a magnetic force in an in-plane configuration with respect to the ultrasound device at a first point in time and an out-of-plane configuration with respect to the ultrasound device at a second point in time that is distinct from the first point in time, the in-plane configuration being distinct from the out-of-plane configuration,
a coupling mechanism configured to couple the first member to the second member such that the first and second members are configured to be movable relative to one another to adjust at least one angle of the electronic device relative to the ultrasound device while the electronic device is positioned in the in-plane configuration with respect to the ultrasound device at the first point in time and while the electronic device is positioned in the out-of-plane configuration, distinct from the in-plane configuration, with respect to the ultrasound device at the second point in time;
a release mechanism configured to release the first assembly from being coupled with the second assembly, wherein the release mechanism comprises a switch; and
a locking component configured to lock the first member and the second member in a position relative to one another,
wherein when the first assembly is released from being coupled with the second assembly via the release mechanism, the first assembly continues to receive the ultrasound device, the second assembly continues to receive and hold by way of only the magnetic force the electronic device, and the ultrasound device and electronic device remain electronically coupled;
the first member includes: (i) an opening for receiving the ultrasound device and (ii) a slot that is separate from the opening, wherein:
the mount includes a cable-management component configured to hold a cable that communicatively and electronically connects the ultrasound device to the electronic device to enable the ultrasound device to provide the imaging data to the electronic device, and
the slot that is separate from the opening is configured such that the cable that communicatively and electronically couples the ultrasound device to the electronic device passes through the slot when the cable is electronically connecting the ultrasound device to the electronic device; and
performing a second ultrasound procedure with another hand of the operator concurrently with the first ultrasound procedure.

15. The method of claim 14, wherein performing the second ultrasound procedure includes utilizing the imaging data of the patient displayed by the electronic device to complete the second ultrasound procedure.

16. The method of claim 15, wherein operating the mount to perform the first ultrasound procedure includes moving or holding the ultrasound device and the electronic device together in one hand while using the other hand to ergonomically perform the second ultrasound procedure.

\* \* \* \* \*